(12) United States Patent
LaBelle et al.

(10) Patent No.: US 10,967,154 B2
(45) Date of Patent: Apr. 6, 2021

(54) ADJUSTABLE GUIDEWIRE

(71) Applicant: ARIZONA BOARD OF REGENTS ON BEHALF OF ARIZONA STATE UNIVERSITY, Scottsdale, AZ (US)

(72) Inventors: Jeffrey LaBelle, Tempe, AZ (US); Julio Morera, Tempe, AZ (US); Marco Santello, Gilbert, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 270 days.

(21) Appl. No.: 16/078,388

(22) PCT Filed: Feb. 21, 2017

(86) PCT No.: PCT/US2017/018638
§ 371 (c)(1),
(2) Date: Aug. 21, 2018

(87) PCT Pub. No.: WO2017/147041
PCT Pub. Date: Aug. 31, 2017

(65) Prior Publication Data
US 2019/0054277 A1    Feb. 21, 2019

Related U.S. Application Data

(60) Provisional application No. 62/298,096, filed on Feb. 22, 2016.

(51) Int. Cl.
*A61M 25/09* (2006.01)

(52) U.S. Cl.
CPC ........ *A61M 25/09* (2013.01); *A61M 25/0905* (2013.01); *A61M 25/09033* (2013.01);
(Continued)

(58) Field of Classification Search
CPC ................ A61M 2025/0915; A61M 2025/09058–09191; A61M 2205/0266;
(Continued)

(56) References Cited

U.S. PATENT DOCUMENTS

| 5,269,759 | A | 12/1993 | Hernandez et al. |
| 5,606,979 | A | 3/1997 | Hodgson |

(Continued)

FOREIGN PATENT DOCUMENTS

| WO | 2014089273 A1 | 6/2014 |
| WO | 2015183893 A1 | 12/2015 |

(Continued)

OTHER PUBLICATIONS

Author Unknown, "Gordis Steerable Guidewire Portfolio," Jun. 2012, Cordis Europe, 19 pages.
(Continued)

*Primary Examiner* — Thaddeus B Cox
(74) *Attorney, Agent, or Firm* — Withrow & Terranova, P.L.L.C.

(57) ABSTRACT

Guidewires useful for cooperating with catheters may be actively steered and/or provide adjustable stiffness. Angle or curvature of a guidewire, and/or flexural modulus of a guidewire, may be adjusted at one or more locations between ends thereof. Variable stiffness segments may include electrically operated compressible and/or extensible materials. Multiple tensile elements may terminate at different body elements to adjust angle or curvature at multiple locations. Multiple circumferentially and/or radially contractible fiber regions may be provided and distributed over a length of a guidewire. Adjustable flexure elements arranged in or along a guidewire may be electrically operated. A flexible core member may be centrally arranged in a (Continued)

tubular body. A flexible guide wire or track may cooperate with electrically operable motor units.

6 Claims, 25 Drawing Sheets

(52) U.S. Cl.
CPC ............ *A61M 2025/09083* (2013.01); *A61M 2025/09133* (2013.01); *A61M 2025/09158* (2013.01); *A61M 2205/0266* (2013.01); *A61M 2205/0272* (2013.01); *A61M 2205/0283* (2013.01); *A61M 2205/0294* (2013.01); *A61M 2205/8262* (2013.01)

(58) Field of Classification Search
CPC .. A61M 2205/0283; A61M 2205/0294; A61M 25/09–0905
See application file for complete search history.

(56) References Cited

U.S. PATENT DOCUMENTS

| | | | |
|---|---|---|---|
| 5,827,201 | A | 10/1998 | Samson et al. |
| 7,018,346 | B2 | 3/2006 | Griffin et al. |
| 7,141,024 | B2 | 11/2006 | Gaber |
| 8,551,019 | B1 | 10/2013 | Kroll |
| 10,219,918 | B2 | 3/2019 | LaBelle et al. |
| 10,323,008 | B2 | 6/2019 | LaBelle et al. |
| 2003/0236445 | A1 | 12/2003 | Couvillon, Jr. |
| 2006/0127561 | A1 | 6/2006 | Griffin et al. |
| 2007/0038237 | A1* | 2/2007 | Swayze .............. A61B 1/00156 606/191 |
| 2007/0250036 | A1* | 10/2007 | Volk .................. A61M 25/0158 604/510 |
| 2008/0091172 | A1 | 4/2008 | Toyoda et al. |
| 2009/0036832 | A1* | 2/2009 | Skujins ................ A61M 25/09 604/164.01 |
| 2009/0082723 | A1* | 3/2009 | Krogh ..................... A61L 29/14 604/95.05 |
| 2010/0305477 | A1 | 12/2010 | Von Weymam-Scharli |
| 2011/0166566 | A1 | 7/2011 | Gabriel |
| 2012/0219744 | A1* | 8/2012 | Walker ...................... B32B 1/08 428/36.91 |
| 2013/0123692 | A1* | 5/2013 | Zhang ................... A61L 31/048 604/95.05 |
| 2014/0180089 | A1* | 6/2014 | Alpert ............... A61M 25/0158 600/438 |
| 2014/0228680 | A1 | 8/2014 | Fukuda |
| 2014/0276899 | A1 | 9/2014 | Novak |
| 2017/0202691 | A1 | 7/2017 | LaBelle et al. |
| 2018/0049897 | A1 | 2/2018 | Lathers et al. |
| 2019/0160206 | A1 | 5/2019 | Lathers et al. |
| 2019/0234816 | A1 | 8/2019 | Labelle et al. |
| 2019/0330163 | A1 | 10/2019 | LaBelle et al. |

FOREIGN PATENT DOCUMENTS

| | | |
|---|---|---|
| WO | 2015188107 A1 | 12/2015 |
| WO | 2015188107 A8 | 12/2015 |
| WO | 2018067626 A1 | 4/2018 |

OTHER PUBLICATIONS

Author Unknown, "Deflectable & Steerable Catheter Handbook: Terminology Guide & Design Options," Retrieved Jan. 15, 2016 from www.creganna.com/wp-content/uploads/Steeringand-DeflectionTerminologyrev3.pdf, Creganna Tactx Medical, 7 pages.
Harrison, G. et al., "Guidewire Stiffness: What's in a Name?" Journal of Endovascular Therapy, vol. 18, 2011, International Society of Endovascular Specialists, pp. 797-801.
McKnight, G. et al., "Segmented Reinforcement Variable Stiffness Materials for Reconfigurable Surfaces," Journal of Intelligent Material Systems and Structures, vol. 21, Nov. 2010, pp. 1783-1793.
International Search Report and Written Opinion for International Patent Application No. PCT/US2017/018638, dated Jun. 27, 2017, 10 pages.
International Preliminary Report on Patentability for International Patent Application No. PCT/US2017/018638, dated Sep. 7, 2018, 7 pages.
U.S. Appl. No. 16/700,621.

\* cited by examiner

| Configuration | Prototype | Number of Wires | Overall Diameter |
|---|---|---|---|
| 50 → 52, 54, 56 | A | 7 | 0.045 in. (1.14 mm) |
| 60 → 62, 64, 65, 66 | B | 7, Coated with PO Shrink Tubing | 0.067 in. (1.70 mm) |
| 70 → 72, 74, 76, 78 | C | 19 | 0.075 in. (1.91 mm) |
| 80 → 82, 84, 86, 87, 88 | D | 19, Coated with PO Shrink Tubing | 0.091 in. (2.31 mm) |
| 90 → 92, 94, 96, 98, 99 | E | 19, Wrapped with SS Spring | 0.125 in. (3.18 mm) |

*FIG. 4*

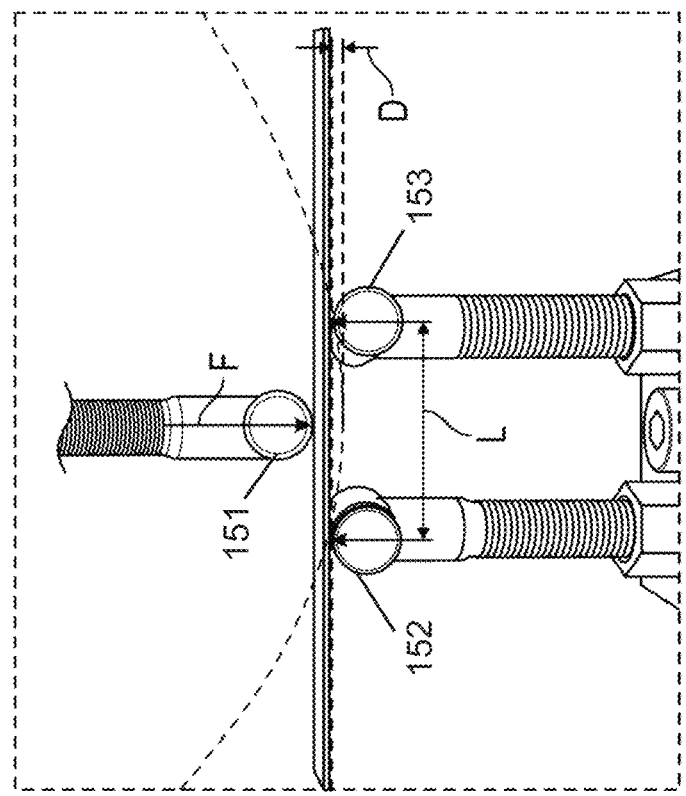
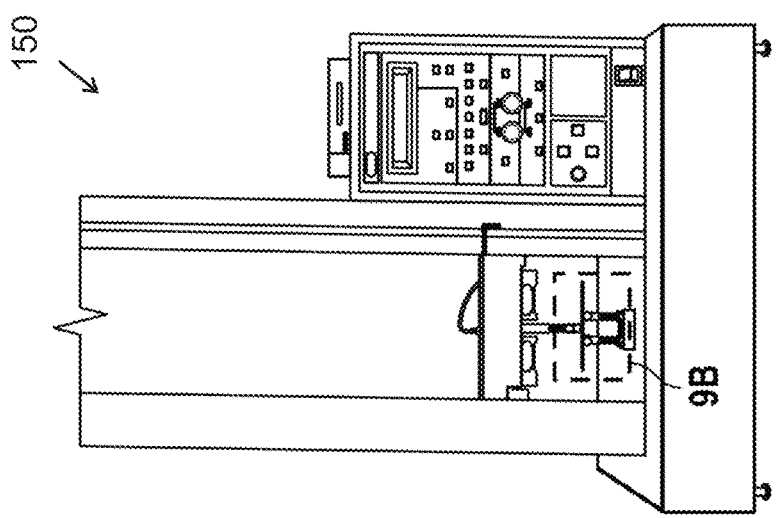
FIG. 9B
FIG. 9A

Results- Deformation-Holding Test

| Starting (mm) | Retained (mm) | | | |
|---|---|---|---|---|
| | Prototype A (7-Wires) | | Prototype C (19-Wires) | |
| Displacement | Radius of Curvature | Displacement | Radius of Curvature | Displacement | Radius of Curvature |
| 1 | 133.3 | 0.94 | 141.8 | 0.70 | 190.5 |
| 2 | 66.7 | 1.67 | 79.8 | 1.74 | 76.8 |
| 3 | 44.4 | 2.00 | 66.7 | 1.54 | 86.6 |
| 4 | 33.3 | 2.13 | 62.7 | 1.26 | 105.8 |
| 5 | 26.7 | 1.99 | 67.1 | 1.14 | 116.6 |
| 6 | 22.2 | 0.88 | 151.5 | 0.75 | 177.8 |

*FIG. 16*

Results Summary

|  |  | Prototype A | Prototype B | Prototype C | Prototype D | Prototype E |
|---|---|---|---|---|---|---|
| $E_f$, Stiff State | FEA | 134.0 GPa | 27.68 GPa | 119.6 GPa | 56.98 GPa | - |
|  | Physical | 84.94 GPa | 16.90 GPa | 68.85 GPa | 25.40 GPa | 17.87 GPa |
| $E_f$, Floppy State | FEA | 16.79 GPa | 5.036 GPa | 6.073 GPa | 3.011 GPa | - |
|  | Physical | 16.78 GPa | 3.857 GPa | 6.782 GPa | 3.297 GPa | 2.583 GPa |
| Stiff State Adhesion Failure | Displacement (Radius of Curvature) at Failure | 0.48 mm (69.4 mm) | 0.37 mm (90.1 mm) | 0.435 mm (76.6 mm) | 0.28 mm (119 mm) | 0.15 mm (222 mm) |
|  | Force | 2.8 N | 2.0 N | 13.2 N | 7.2 N | 11.2 N |
| Minimum Radius of Curvature | Calculated Based on Material Properties of Wires | 21-23 mm | | | | |

FIG. 17

| Specification | Target Value | Prototype A | Prototype C | Scaled Down Prediction (Based on a 19-Wire Design) |
|---|---|---|---|---|
| Diameter | 0.035 in (0.889 mm) | 0.045 in (1.143 mm) | 0.075 in (1.905 mm) | 0.035 in (0.889 mm) |
| Wire Element Diameter | | 0.015 in (0.381 mm) | 0.015 in (0.381 mm) | 0.007 in (0.1778 mm) |
| Flexural Modulus, Controllable | 9.5 GPa - 160 GPa | 16.78 GPa - 84.94 GPa | 6.782 GPa - 68.85 GPa | 6.782 GPa - 68.85 GPa |
| Minimum Radius of Curvature without Plastic Deformation | 5 mm - 10 mm | 23 mm | 23 mm | 10.7 mm (ASTM 228) 7.7 mm (302 SS) |
| Maintains Position/ Shape During Stiffness Change | Yes | Yes | Yes | Yes |

*FIG. 18*

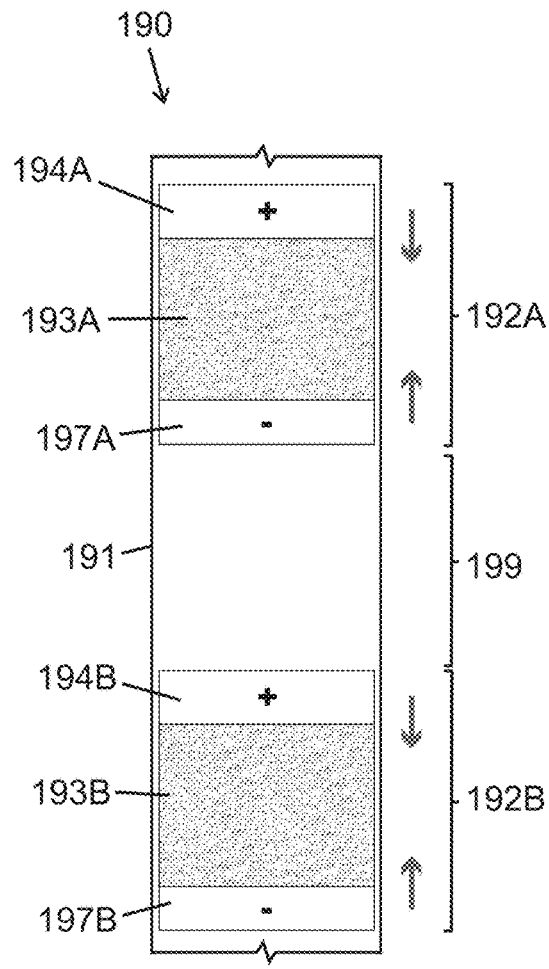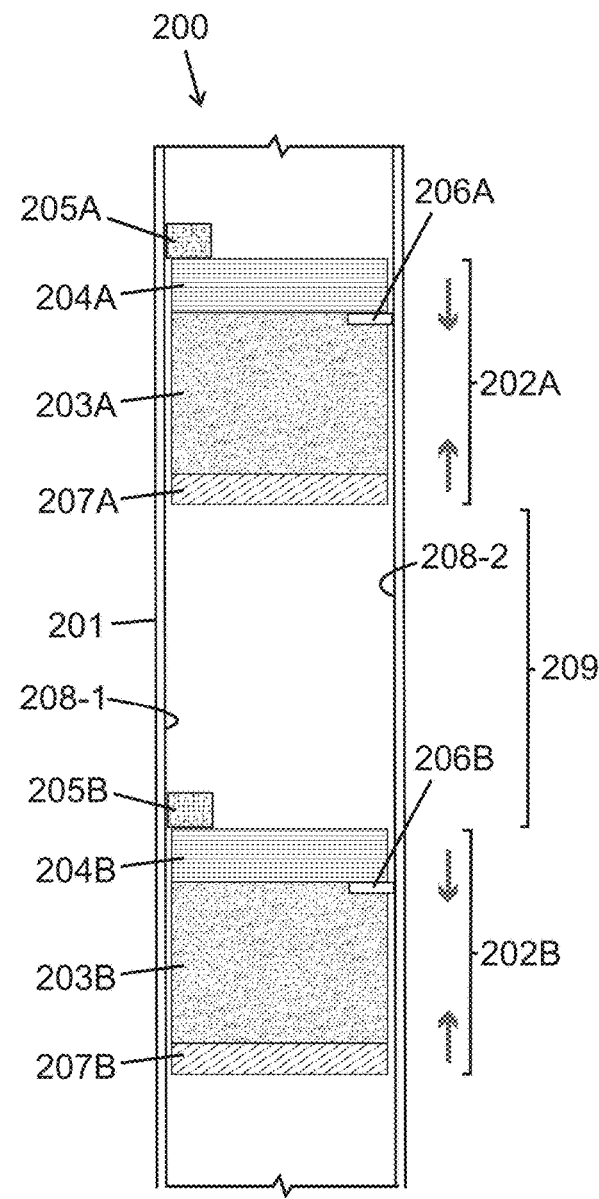
FIG. 22A
FIG. 22B

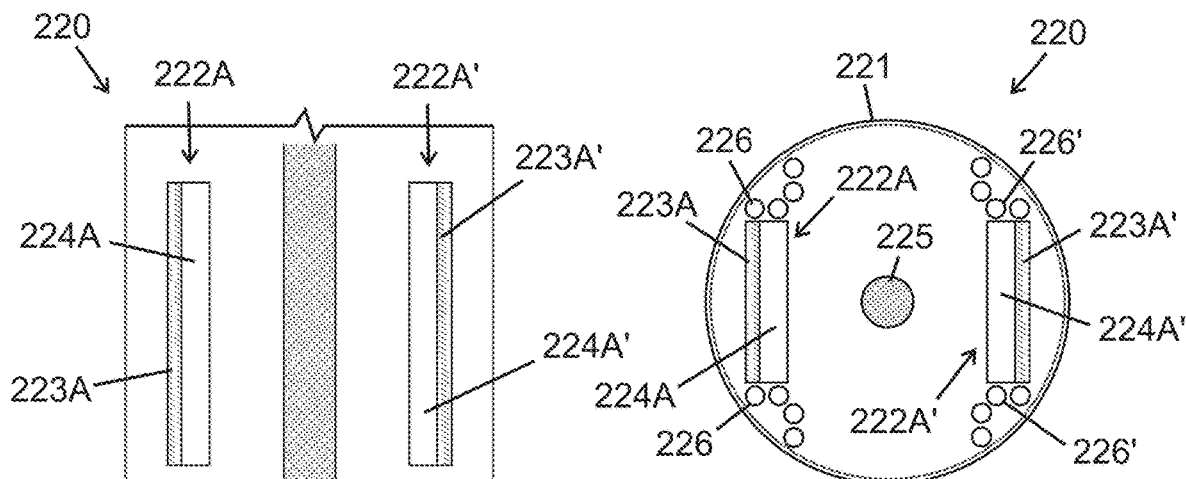
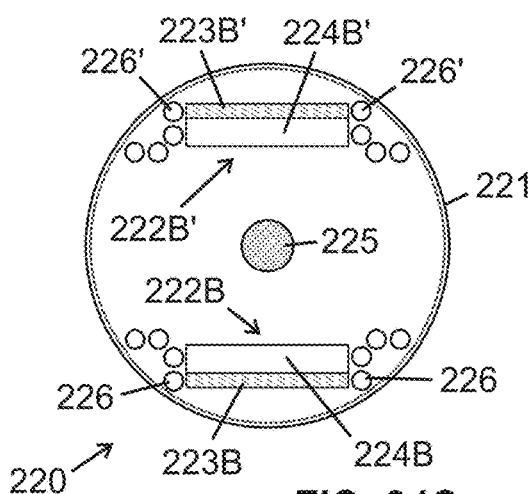
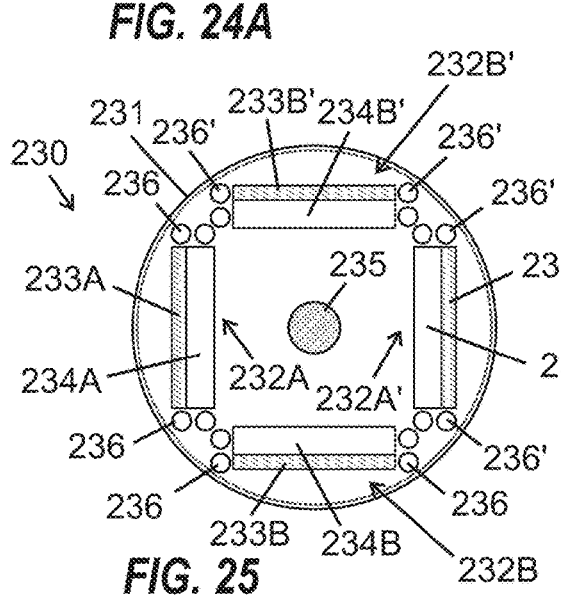
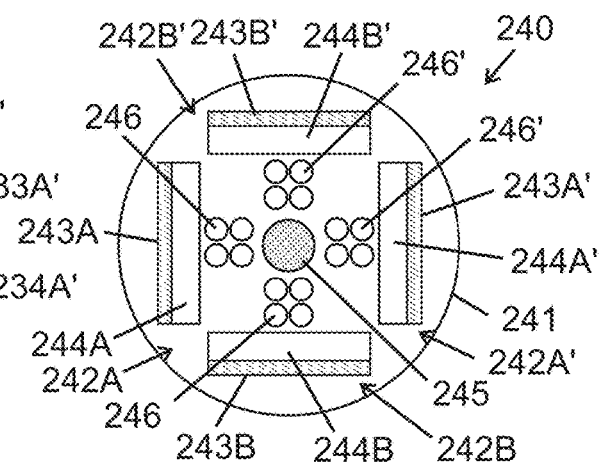
FIG. 24A  FIG. 24B  FIG. 24C  FIG. 25  FIG. 26

ADJUSTABLE GUIDEWIRE

STATEMENT OF RELATED APPLICATION(S)

This application is a 35 U.S.C. § 371 national phase filing of International Application No. PCT/US2017/018638 filed on Feb. 21, 2017, and claims the benefit of U.S. Provisional Patent Application No. 62/298,096 filed on Feb. 22, 2016, wherein the disclosures of the foregoing applications are hereby incorporated by reference herein in their respective entireties.

TECHNICAL FIELD

This disclosure relates to guidewires being insertable into internal sites of mammalian bodies, and being useful for inserting, positioning, and moving catheters for diagnostic procedures, therapeutic procedures, and/or delivering therapeutic agents.

BACKGROUND

Catheters are used for performing diagnostic procedures and for delivering therapeutic agents to internal sites within a human body that can be accessed through various lumen systems, such as the vasculature. A guidewire is a device used to enter tight spaces (e.g., obstructed or tortuous passages) within the body, or to assist in inserting, positioning, and moving a catheter—such as through bends and branches of blood vessels. Guidewires vary in size, length, stiffness, composition, and tip shape. A conventional guidewire may include a slight bend at its distal end, and may be guided by selective rotation and advancement along a pathway to a desired target location. Thereafter, the guidewire may be held in place, and a catheter may be advanced along a longitudinal axis of the guidewire.

Insertion of a guidewire into a vessel lumen is schematically illustrated in FIG. 1A. A guidewire 10 is advanced into a target vessel lumen 12, which may include multiple bends or turns 14, 16. As shown in FIG. 1B, the guidewire 10 is deflected as it is pushed forward against walls of the vessel lumen 12. Thereafter, as shown in FIG. 1C, a catheter 18 is advanced over the guidewire 10, which provides a stable support during advancement.

A side cross-sectional schematic view of a portion of a conventional flexible guidewire 20 is shown in FIG. 2. A distal portion of the guidewire 20 includes a tip 22 (which may be convex along its outer perimeter) to which a longitudinal core wire or mandrel 24 and a safety ribbon wire embodied in a flexible coil 26 (e.g., distal coil) are attached. The core wire or mandrel 24 may include a constant diameter portion 24A over much of its length, as well as first and second reduced diameter portions 24B, 24C between the constant diameter portion 24A and the tip 22. As shown in FIG. 2, an external coating 28 may be provided over the constant diameter portion 24A of the longitudinal core wire or mandrel 24, and the flexible coil 26 may be provided over the first and second reduced diameter portion(s) 24B, 24C between the coated constant diameter portion 24A and the tip 22. The flexible coil 26 may be generally helical in shape, similar to a spring. A proximal coil portion 26A including a first (e.g., smaller) coil pitch may extend over the first reduced diameter portion 24B of the core wire or mandrel 24, and a distal coil portion 26B including a second (e.g., larger) coil pitch may extend over the second reduced diameter portion 24C of the core wire or mandrel 24, wherein the second reduced diameter portion 24C of the core wire or mandrel 24 has a smaller diameter than the first reduced diameter portion 24B. Relative to the coated constant diameter portion 24A, increased flexibility is provided by the first reduced diameter portion 24B of the core wire or mandrel 24 covered by the proximal coil portion 26A, and still further increased flexibility is provided by the second reduced diameter portion 24C of the core wire or mandrel 24 covered by the distal coil portion 26B. The guidewire 20 is therefore tapered along its length, with decreasing diameter sections toward the tip 22 to reduce stiffness to allow for better steerability. Thus, the guidewire 20 has flexibility that increases with proximity to the tip 22, and stiffness that increases with increasing distance away from the tip 22. As further shown in FIG. 2, the outside diameter of each of the external coating 28, the proximal coil portion 26A, and the distal coil portion 26B may be substantially the same. The external coating 28 provides lubricity for navigation and for delivering catheters, and may include materials such as PTFE, polyurethanes, or silicone-based materials, that are preferably hydrophilic in nature. A coating may further include Heparin or other therapeutic agents to reduce thrombogenicity.

Maneuvering a guidewire within the body can be difficult. At least a certain degree of flexibility is necessary or desirable for most applications, but a guidewire must also maintain sufficient stiffness to provide support to permit advancement of a catheter. A static guidewire 20 such as illustrated in FIG. 2 may have regions with differing flexibility and stiffness properties proximate to the tip 22, but such properties are established during manufacture (therefore fixed with respect to time) and are not subject to temporal alteration (e.g., with respect to degree and/or position). Since stiffness of a static guidewire cannot be changed, a guidewire must be exchanged with another wire if a different stiffness is needed, thereby prolonging a surgical procedure with concomitant risk to the patient. Examples of conventional static guidewires (which come in various lengths, stiffnesses, and configurations) include LUNDERQUIST® Extra Stiff (Cook Inc., Bloomington, Ind., US), Amplatz™, and ASAHI INTECC® Standard (Asahi Intecc Co., Ltd., Nagoya, JP), among others.

Moveable core guidewires have been developed, such as the NAMIC® Angiographic Core Guidewire (North American Instrument Corp., Hudson Falls, N.Y., US) and the STARTER™ moveable core guidewire (Boston Scientific Scimed, Inc., Maple Grove, Minn., US). In certain instances, moveable core guidewires can change stiffness by moving a core wire within an outer coil. With the core removed, the remaining outer coil provides a flexible and generally atraumatic tip. A moveable core allows for changing a curvature of a J-shaped tip to aid in branch selection. However, frictional forces may render it difficult to move a core through an outer coil when the guidewire is positioned in a tightly curved path, and movement of a core relative to an outer coil also entails the risk that a core may inadvertently stab through a coil, thereby risking puncture of adjacent tissue. Safe core movement is typically limited to the most distal 10 cm (proximate to a tip) of a moveable core guidewire. Generally, moveable core guidewires have outer diameters of at least about 0.035 inch (0.89 mm) and tend to straighten when stiffness is increased.

Conventional guidewires may range in outer diameter from about 0.014 inch (0.36 mm) to about 0.038 inch (0.97 mm) (with smaller values corresponding to static guidewires), and may vary in length from about 45 cm to about 260 cm or more. Depending on the core material, a conventional static guidewire may have a minimum radius of curvature of from about 18 mm to about 40 mm, and a movable core guidewire may have a minimum radius of curvature (without deformation of the metal core) of from about 2 mm (e.g., in a state with the core removed) to about 18 mm (e.g., in a state with the core in place).

Guidewires that permit a certain degree of steerability have been developed, such as disclosed in International Patent Application Publication No. WO 2014/089273 A1 to Lenker et al. Additionally, guidewires with adjustable flexibility or stiffness are known, such as disclosed in U.S. Pat. No. 7,018,346 B2 to Griffin et al. and U.S. Pat. No. 8,551,019 B1 to Kroll.

Despite various developments in the guidewire art, the art continues to seek advancements in guidewires that may be actively steered and/or provide adjustable flexibility, to facilitate precise and rapid placement of a catheter in a desired location within a body.

SUMMARY

The present disclosure relates to guidewires that may be actively steered and/or provide adjustable stiffness. Active steering may include adjustment of an angle and/or curvature of a guidewire at one or more locations between a first end and a second end thereof. Adjustable stiffness may include adjustment of flexural modulus at one or more locations between a first end and a second end thereof. A guidewire with controllable stiffness may fulfill the roles of both floppy and stiff guidewires during a procedure, thereby obviating the need for guidewire exchange.

In one aspect, a guidewire device includes a tube having a longitudinal axis and an interior; and at least one variable stiffness segment arranged within the interior of the tube, wherein the at least one variable stiffness segment includes an electromagnet, at least one magnetically responsive element, and a compressible and/or extensible material arranged between the electromagnet and the at least one magnetically responsive element. In the at least one variable stiffness segment, the electromagnet is configured to receive at least one electrical signal to selectively generate a magnetic field sufficient to interact with the at least one magnetically responsive element, thereby exerting a compression or extension force on the compressible and/or extensible material to adjust a stiffness of the at least one variable stiffness segment.

In certain embodiments, the at least one variable stiffness segment comprises a plurality of variable stiffness segments that are sequentially arranged along the longitudinal axis. In certain embodiments, each variable stiffness segment of the plurality of variable stiffness segments is independently controllable. In certain embodiments, the compressible and/or extensible material includes a foam material. In certain embodiments, the at least one magnetically responsive element includes at least one metal element.

In certain embodiments, the guidewire device further includes a plurality of electrical conductors arranged in or on the tube and operatively coupled with the at least one variable stiffness segment to supply the at least one electrical signal. In certain embodiments, a plurality of circumferentially contractible fiber regions is arranged in or on the tube, wherein each circumferentially contractible fiber region of the plurality of circumferentially contractible fiber regions is longitudinally spaced from each other circumferentially contractible fiber region. In certain embodiments, a plurality of radially contractible fiber regions is arranged in or on the tube, wherein each radially contractible fiber region of the plurality of radially contractible fiber regions is longitudinally spaced from each other radially contractible fiber region. In certain embodiments, the tube includes a polymer adhesive, and the guidewire device includes at least one electrical conductor configured to be coupled with an electric power source for resistive heating of the polymer adhesive to adjust a stiffness property of the polymer adhesive.

In another aspect, a guidewire device includes a tube having a longitudinal axis, a first end, a second end, and an interior; a plurality of body elements and a plurality of pivot joints sequentially arranged in a longitudinal direction within the interior of the tube between the first end and the second end, wherein each body element of the plurality of body elements is connected to at least one other body element via at least one pivot joint of the plurality of pivot joints; and a plurality of tensile elements extending in the longitudinal direction through the tube from the first end toward the plurality of body elements. Different tensile elements of the plurality of tensile elements terminate at different body elements of the plurality of body elements, and are separately operable to cause pivotal movement between different body elements of the plurality of body elements, thereby permitting adjustment of an angle or curvature of the guidewire device at multiple positions along the longitudinal axis.

In certain embodiments, the plurality of tensile elements includes at least one agonist tensile element and at least one antagonist tensile element, wherein the at least one antagonist tensile element is configured to be operated to counteract the at least one agonist tensile element to control pivotal movement between different body elements of the plurality of body elements. In certain embodiments, the plurality of tensile elements are operatively connected to a plurality of tensioning elements configured to selectively apply tension to different tensile elements of the plurality of tensile elements. In certain embodiments, the plurality of tensioning elements are arranged beyond the first or second end of the tube.

In certain embodiments, a plurality of circumferentially contractible fiber regions is arranged in or on the tube, wherein each circumferentially contractible fiber region of the plurality of circumferentially contractible fiber regions is longitudinally spaced from each other circumferentially contractible fiber region. In certain embodiments, each circumferentially contractible fiber region of the plurality of circumferentially contractible fiber regions comprises an electrically responsive material selected from the group consisting of a piezoelectric material, an electroactive polymer, and a nitinol alloy.

In certain embodiments, a plurality of radially contractible fiber regions is arranged in or on the tube, wherein each radially contractible fiber region of the plurality of radially contractible fiber regions is longitudinally spaced from each other radially contractible fiber region. In certain embodiments, each radially contractible fiber region of the plurality of radially contractible fiber regions comprises an electrically responsive material selected from the group consisting of a piezoelectric material, an electroactive polymer, and a nitinol alloy.

In certain embodiments, the tube comprises a polymer adhesive, and the guidewire device includes at least one electrical conductor configured to be coupled with an electric power source for resistive heating of the polymer adhesive to adjust a stiffness property of the polymer adhesive.

In another aspect, a guidewire device includes a tubular body having a longitudinal axis, a first end, a second end, and an interior; a plurality of longitudinally contractible fiber regions arranged in or on the tubular body, wherein each longitudinally contractible fiber region of the plurality of longitudinally contractible fiber regions is laterally spaced from each other longitudinally contractible fiber region; and a plurality of circumferentially contractible fiber regions arranged in or on the tubular body, wherein each circumferentially contractible fiber region of the plurality of circumferentially contractible fiber regions is longitudinally spaced from each other circumferentially contractible fiber region. Different longitudinally contractible fiber regions of the plurality of longitudinally contractible fiber regions are separately operable to adjust an angle or curvature of the guidewire device between the first end and the second end; and different circumferentially contractible fiber regions of the plurality of circumferentially contractible fiber regions are separately operable to locally adjust a stiffness of the tubular body.

In certain embodiments, each circumferentially contractible fiber region of the plurality of circumferentially contractible fiber regions includes an electrically responsive material selected from the group consisting of a piezoelectric material, an electroactive polymer, and a nitinol alloy. In certain embodiments, each longitudinally contractible fiber region of the plurality of longitudinally contractible fiber regions includes an electrically responsive material selected from the group consisting of a piezoelectric material, an electroactive polymer, and a nitinol alloy.

In certain embodiments, a plurality of radially contractible fiber regions are arranged in or on the tubular body, wherein each radially contractible fiber region of the plurality of radially contractible fiber regions is longitudinally spaced from each other radially contractible fiber region. In certain embodiments, each radially contractible fiber region of the plurality of radially contractible fiber regions includes an electrically responsive material selected from the group consisting of a piezoelectric material, an electroactive polymer, and a nitinol alloy. In certain embodiments, the tubular body includes a polymer adhesive, and the guidewire device includes at least one electrical conductor configured to be coupled with an electric power source for resistive heating of the polymer adhesive to adjust a stiffness property of the polymer adhesive.

In another aspect, a guidewire device includes a tubular body having a longitudinal axis, a first end, a second end, and an interior; and a plurality of adjustable flexure elements arranged in or on the tubular body; wherein the plurality of adjustable flexure elements are electrically operable to adjust an angle or curvature of the guidewire device between the first end and the second end. In certain embodiments, the plurality of adjustable flexure elements includes at least one pair of adjustable flexure elements including first and second opposing flexure elements arranged at different lateral positions relative to the tubular body. In certain embodiments, the at least one pair of adjustable flexure elements includes a first pair of adjustable flexure elements and a second pair of adjustable flexure elements, wherein the first pair of adjustable flexure elements and the second pair of adjustable flexure elements are arranged at different longitudinal positions relative to the tubular body.

In certain embodiments, each adjustable flexure element of the plurality of adjustable flexure elements is electrically operable. In certain embodiments, each adjustable flexure element of the plurality of adjustable flexure elements includes an electrically responsive material selected from the group consisting of a piezoelectric material, an electroactive polymer, and a nitinol alloy. In certain embodiments, each adjustable flexure element of the plurality of adjustable flexure elements further includes a coating layer or backbone layer arranged in contact with the electrically responsive material. In certain embodiments, the guidewire device includes a plurality of conductors in electrical communication with the plurality of adjustable flexure elements. In certain embodiments, at least one adjustable flexure element of the plurality of adjustable flexure elements is independently controllable relative to at least one other adjustable flexure element of the plurality of adjustable flexure elements.

In certain embodiments, a plurality of circumferentially contractible fiber regions is arranged in or on the tubular body, wherein each circumferentially contractible fiber region of the plurality of circumferentially contractible fiber regions is longitudinally spaced from each other circumferentially contractible fiber region. In certain embodiments, each circumferentially contractible fiber region of the plurality of circumferentially contractible fiber regions includes an electrically responsive material selected from the group consisting of a piezoelectric material, an electroactive polymer, and a nitinol alloy.

In certain embodiments, a plurality of radially contractible fiber regions is arranged in or on the tubular body, wherein each radially contractible fiber region of the plurality of radially contractible fiber regions is longitudinally spaced from each other radially contractible fiber region. In certain embodiments, each radially contractible fiber region of the plurality of radially contractible fiber regions includes an electrically responsive material selected from the group consisting of a piezoelectric material, an electroactive polymer, and a nitinol alloy. In certain embodiments, the tubular body includes a polymer adhesive, and the guidewire device includes at least one electrical conductor configured to be coupled with an electric power source for resistive heating of the polymer adhesive to adjust a stiffness property of the polymer adhesive.

In another aspect, a guidewire device includes a tube having a longitudinal axis, a first end, a second end, and an interior; a flexible guide wire or track arranged within the tube; and a plurality of translatable elements arranged to independently translate along the flexible guide wire or track parallel to the longitudinal axis; wherein each translatable element of the plurality of translatable elements is electrically operable to be translated in a longitudinal direction and thereby adjust a stiffness, angle, or curvature of the guidewire device between the first end and the second end. In certain embodiments, each translatable element of the plurality of translatable elements includes an electric motor unit.

In certain embodiments, the electric motor unit of each translatable element of the plurality of translatable elements is controllable by a signal of a different frequency from each other electric motor unit of the guidewire device. In certain embodiments, the flexible guide wire or track includes a plurality of grooves or teeth, and each electric motor unit includes an engagement element arranged to engage with the plurality of grooves or teeth. In certain embodiments, the tube includes a polymer adhesive, and the guidewire device includes at least one electrical conductor configured to be coupled with an electric power source for resistive heating of the polymer adhesive to adjust a stiffness property of the polymer adhesive.

In another aspect, a guidewire device includes a tube having a longitudinal axis, a first end, a second end, and an interior; and a plurality of wires arranged in or on the tube. The tube includes a polymer adhesive, and at least one wire of the plurality of wires is configured to be coupled with an electric power source for resistive heating of the polymer adhesive to adjust a stiffness property of the polymer adhesive.

In certain embodiments, the plurality of wires includes braided wires or multiple wires twisted about a core wire. In certain embodiments, each wire of the plurality of wires includes at least one flat side surface arranged to contact a flat side surface of another wire of the plurality of wires. In certain embodiments, each wire of the plurality of wires includes a polygonal cross-sectional shape. In certain embodiments, each wire of the plurality of wires includes a hexagonal cross-sectional shape. In certain embodiments, at least some wires of the plurality of wires comprise metal. In certain embodiments, at least some wires of the plurality of wires comprise conductive polymer material or composite material.

In certain embodiments, a guidewire device as disclosed herein includes a metal coil spring or flexible metal sheath extending generally parallel to the longitudinal axis and surrounding at least a portion of a tube or tubular element of the guidewire device.

In certain aspects, a diagnostic or therapeutic device includes a catheter as well as a guidewire device as disclosed herein, wherein the catheter is configured to be advanced over the guidewire device.

In certain aspects, a method for diagnosis or therapeutic intervention comprises insertion of a guidewire device as disclosed herein into a lumen system of a mammalian (e.g., human or animal) body, followed by advancement of a catheter over the guidewire device. During such insertion, one or more properties such as stiffness, angle, and/or curvature of the guidewire device may be adjusted at one or more positions between a distal end and proximal end thereof.

In certain aspects, any of the preceding aspects or other features disclosed here may be combined for additional advantage.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

FIG. 4 is a table depicting cross-sectional geometries and identifying numbers of wires and overall diameters for five different bundled wire system prototype designs A-E.

FIG. 9A illustrates an INSTRON® materials testing machine used to apply three point bending to physical samples of bundled wire systems described herein.

FIG. 9B is a magnified view of a portion of the testing machine of FIG. 9A.

FIG. 16 is a table providing numerical results obtained by the deformation-holding test described herein for bundled wire systems according to prototype designs A and C as described in connection with FIG. 4.

FIG. 17 is a table summarizing numerical results of FEA modeled $E_f$ (stiff state), tested (physical) $E_f$ (stiff state), FEA modeled $E_f$ (floppy state), tested (physical) $E_f$ (floppy state), stiff state displacement at adhesion failure, stiff state radius of curvature at adhesion failure, force at stiff state adhesion failure, and minimum radius of curvature for bundled wire systems according to prototype designs A to E as described in connection with FIG. 4.

FIG. 18 is a table summarizing numerical results of flexural modulus and minimum radius of curvature without plastic deformation, as well as observations as to whether shape is maintained during stiffness change, for bundled wire systems according to prototype designs A and C as described in connection with FIG. 4.

FIG. 22A schematically illustrates a portion of a guidewire device in which stiffness at one or more locations may be adjusted by selective operation or modulation of one or more electromagnetic elements, according to one embodiment of the present disclosure.

FIG. 22B schematically illustrates a portion of a guidewire device in which stiffness at one or more locations may be adjusted by selective operation or modulation of one or more electromagnetic elements, including longitudinally extending conductors inset slightly relative to a tubular body, according to one embodiment of the present disclosure.

FIG. 24A is a simplified schematic cross-sectional illustration of a portion of a guidewire device according to one embodiment, including multiple pairs of electrically operable adjustable flexure elements arranged at different locations in or on a tubular body around a longitudinally extended flexible core, wherein angle or radius of curvature at one or more locations may be adjusted by applying current to the pairs of electrically operable adjustable flexure elements.

FIG. 24B is a first cross-sectional illustration of the guidewire device according to FIG. 24A, including a first pair of adjustable flexure elements.

FIG. 24C is a second cross-sectional illustration of the guidewire device of FIG. 24A, including a second pair of adjustable flexure elements.

FIG. 25 is a cross-sectional illustration of a portion of a guidewire device according to one embodiment similar to the device of FIGS. 24A-24C, including multiple pairs of adjustable flexure elements arranged in a tubular body with peripherally arranged electrical conductors, and with first and second pairs of adjustable flexure elements arranged at the same or a similar longitudinal position.

FIG. 26 is a cross-sectional illustration of a portion of a guidewire device according to one embodiment similar to the device of FIG. 25, including multiple pairs of adjustable flexure elements arranged in a tubular body with medially arranged electrical conductors, and with first and second pairs of adjustable flexure elements arranged at the same or a similar longitudinal position.

DETAILED DESCRIPTION

The present disclosure relates to guidewires that may be actively steered and/or provide adjustable stiffness. The term "and/or" as used herein encompasses either or all of multiple stated possibilities. Active steering may include adjustment of an angle and/or curvature of a guidewire at one or more locations between a first end and a second end thereof. Adjustable stiffness may include adjustment of flexural modulus at one or more locations between a first end and a second end thereof.

Guidewires as disclosed herein are intended and suitable for insertion into a vessel lumen system of a mammalian (e.g., human) body, and to provide a stable platform for advancement of catheters for performance of diagnostic and/or therapeutic methods. During such insertion, one or more properties such as stiffness, angle, and/or curvature of the guidewire may be adjusted at one or more positions between a distal end and proximal end thereof.

Figure 1A:
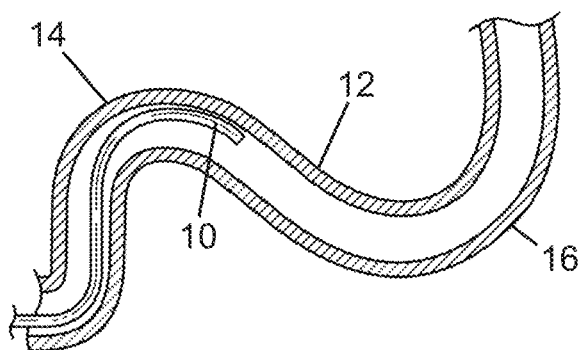
FIG. 1A is a cross-sectional schematic view of a flexible guidewire being advanced past a first curve or bend of a vessel lumen.
Figure 1B:
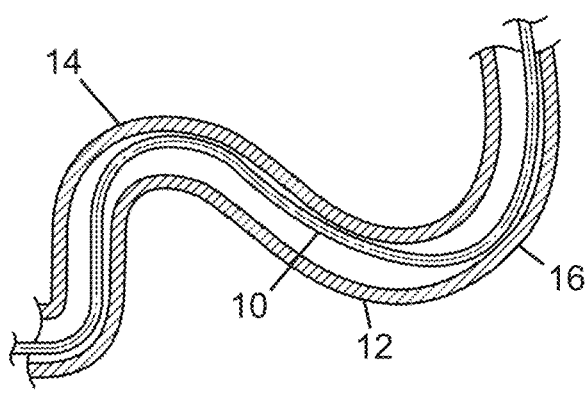
FIG. 1B is a cross-sectional schematic view of the flexible guidewire and vessel lumen of FIG. 1A following advancement of the flexible guidewire past a second curve or bend of the vessel lumen.
Figure 1C:
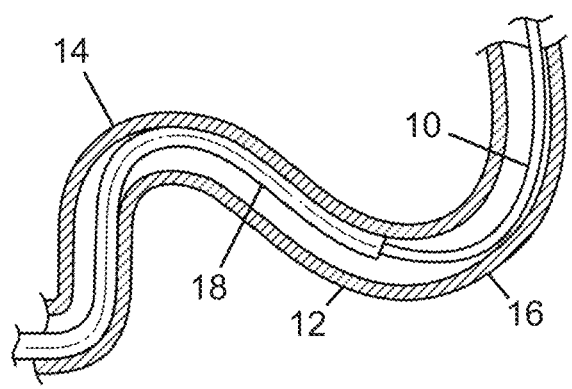
FIG. 1C is a cross-sectional schematic view of the flexible guidewire and vessel lumen of FIGS. 1A and 1B following advancement of a catheter over a portion of the flexible guidewire within the vessel lumen.
Figure 2:
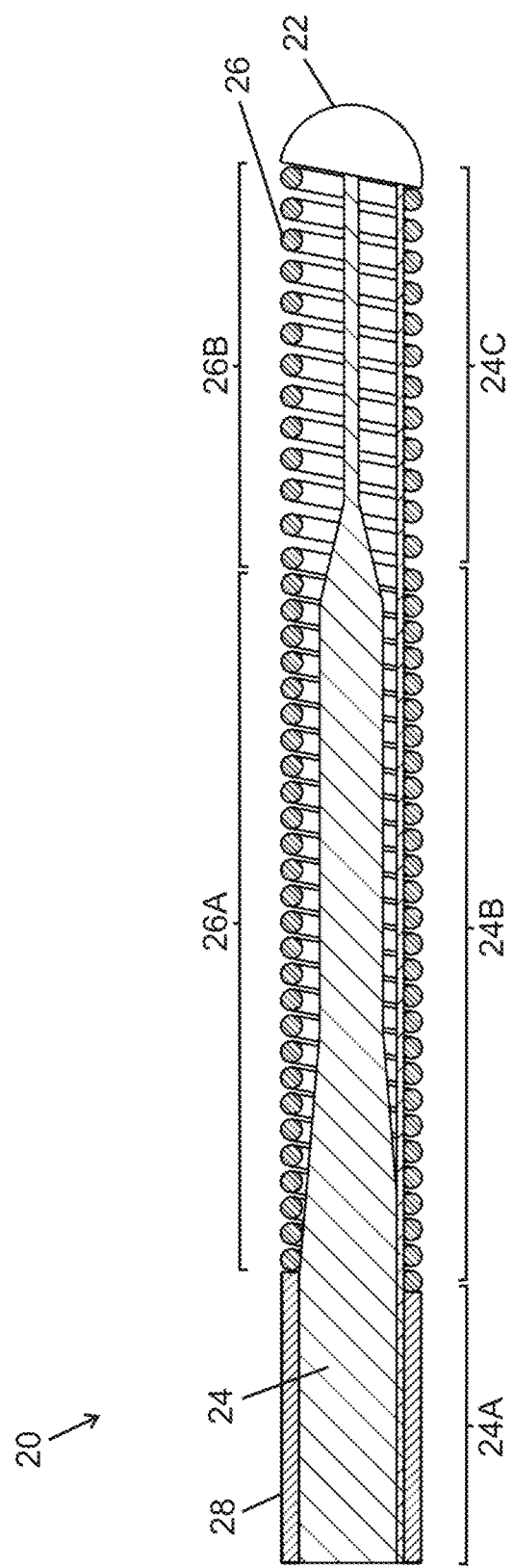
FIG. 2 is a side cross-sectional schematic view of a portion of a conventional flexible guidewire that includes a variable diameter longitudinal core wire or mandrel and a flexible coil arranged over the core wire or mandrel proximate to a distal tip of the guidewire.
Figure 3:
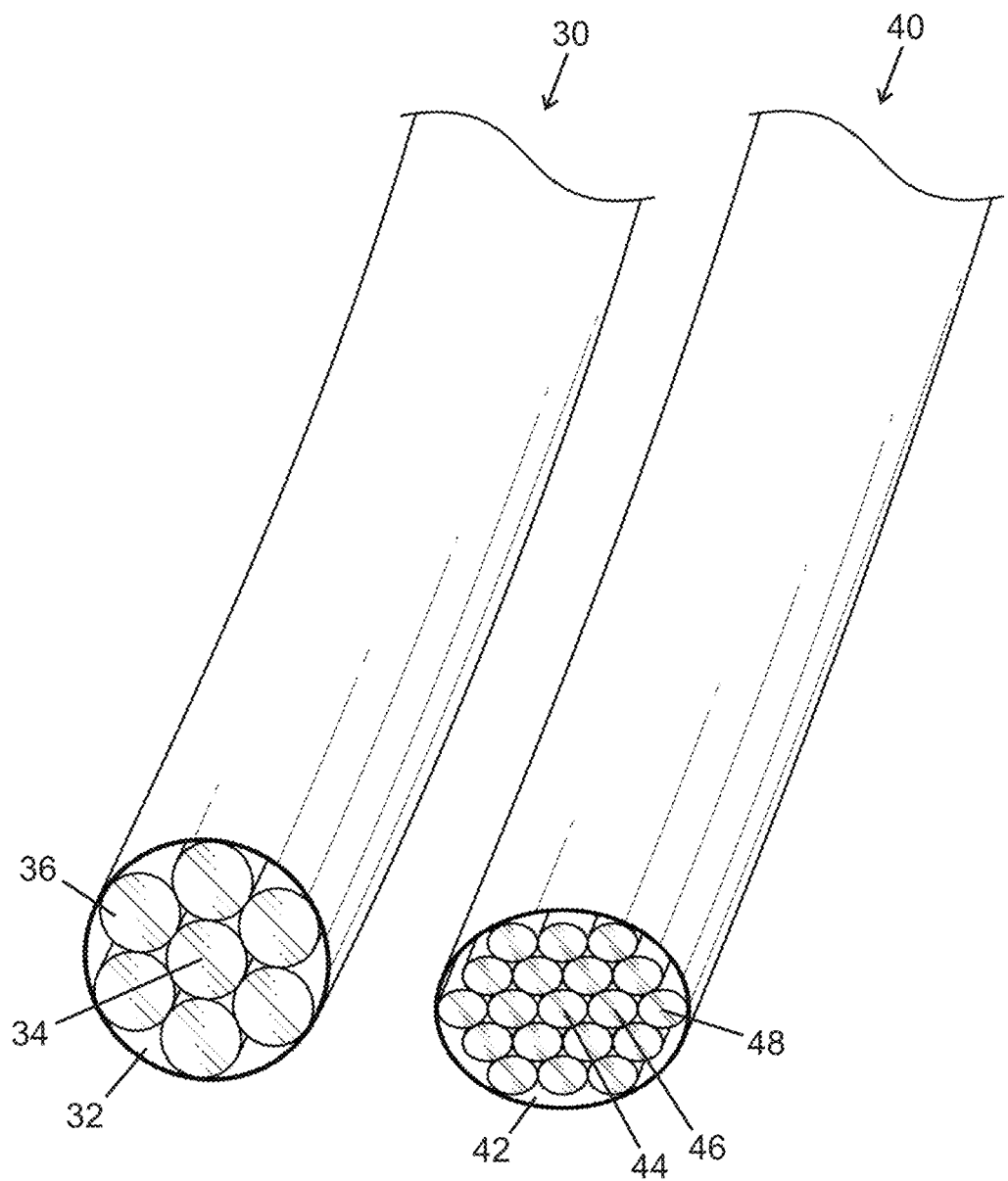
FIG. 3 provides perspective, partial cross-sectional views of first and second conventional bundled wire systems each including multiple wires with adhesive polymer between and around the wires.

To investigate a potential mechanism of action for adjusting stiffness, bundled wire systems held together with low melting point polymer adhesive were modeled and separately tested. Stiffness of each bundle may be controlled by resistive Joule heating, by applying electrical current to the wires to soften (e.g., melt) the polymer adhesive. When in a cool state, a wire bundle is stiff since the polymer firmly couples the wires to one another. However, when heated to a warm state, a wire bundle is floppy in character, since the melted polymer softens and flows, thereby decoupling the wires and permitting the wires to adopt a new geometry. Representative bundled wire systems 30, 40 are illustrated in FIG. 3. At left, FIG. 3 illustrates a bundled seven-wire system 30 with adhesive polymer 32 between and around wires 34, 36, in which a group of six peripheral wires 36 form a single-layer ring around a center wire 34. At right, FIG. 3 illustrates a bundled nineteen-wire system 40 with adhesive polymer 42 between and around multiple wires 44, 46, 48, in which a first group of six wires 46 forms a first ring around a center wire 44, and a second group of twelve wires 48 forms a second ring around the first group of six wires 46, thus forming a double layer bundle. The wires 44, 46, 48 in the double layer bundle of the nineteen-wire system 40 at right are substantially smaller in diameter than the wires 34, 36 in the single layer bundle of the seven-wire system 30 at left. In each instance, close-packed cylindrical bundles are formed of concentric layers of straight wire, with each bundle including wires of uniform size. The stiffness range depends on the number of wires, wherein more wires yield a greater reduction in stiffness, and the minimum radius of curvature depends on individual wire diameter.

FIG. 4 is a table identifying five different bundled wire system prototype designs A to E. Each prototype design used steel music wire (ASTM 228), 0.015 inch (0.38 mm) individual wire diameter, 6 inches (15.2 cm) long, with properties similar to medical grade Type 304 stainless steel as commonly used in guidewires. In each case, a biocompatible adhesive polymer (INSTAMORPH® polycaprolactone (Happy Wire Dog, LLC, Scottsdale, Ariz., US) or "PCL") was used, with such material exhibiting a low melting point of 60° C. A bundled wire system 50 according to the design of Prototype A included seven wires (with six peripheral wires 56 forming a single-layer ring around a center wire 54) embedded in adhesive polymer 52 with an overall diameter of 0.045 inch (1.14 mm). The bundled wire system 60 according to the design of Prototype B included seven wires (with six peripheral wires 66 forming a single-layer ring around a center wire 64) embedded in adhesive polymer 62 and coated with polyolefin (PO) heat shrink tubing 65, yielding an overall diameter of 0.067 inch (1.7 mm). The polyolefin heat shrink tubing 65 was intended to keep the wires 64, 66 bundled together under bending, and to resist the tendency for adhesion to fail. The bundled wire system 70 according to the design of Prototype C included nineteen wires (with a first group of six wires 76 forming a first ring around a center wire 74, and a second group of twelve wires 78 forming a second ring around the first ring) embedded in adhesive polymer 72, with an overall diameter of 0.075 inch (1.91 mm). The bundled wire system 80 according to the design of Prototype D included nineteen wires (with a first group of six wires 86 forming a first ring around a center wire 84, and a second group of twelve wires 88 forming a second ring around the first ring) embedded in adhesive polymer 82 and coated with polyolefin heat shrink tubing 87, yielding an overall diameter of 0.091 inch (2.31 mm). The bundled wire system 90 according to the design of Prototype E included 19 wires (with a first group of six wires 96 forming a first ring around a center wire 94, and a second group of twelve wires 98 forming a second ring around the first ring) embedded in adhesive polymer 92 and wrapped with a stainless steel spring 99, yielding an overall diameter of 0.125 inch (3.18 mm).

The minimum radius (p) of curvature achievable by a wire bundle when bent was calculated as equal to the minimum radius of curvature achievable by the innermost wire before plastically deforming (in other words, when the maximum axial stress in the material reached its yield stress). The minimum radius (p) of curvature is calculated as the product of the flexural modulus of the wire material and the radius of the individual wire, divided by the yield stress.

Figure 5:
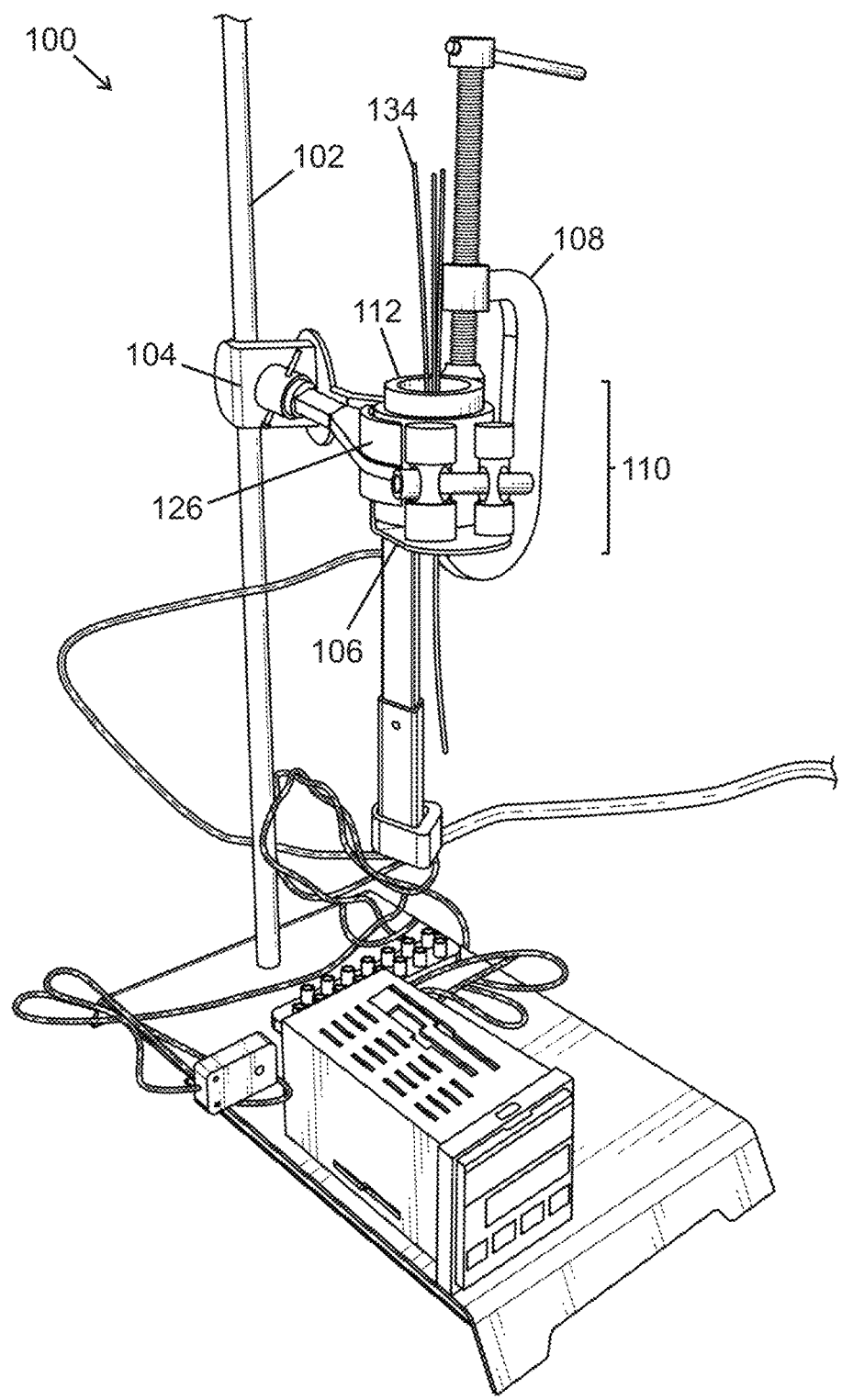
FIG. 5 is a perspective view of a pultruder used to make the bundled wire system prototype designs A-E described in connection with FIG. 4.
Figure 6:
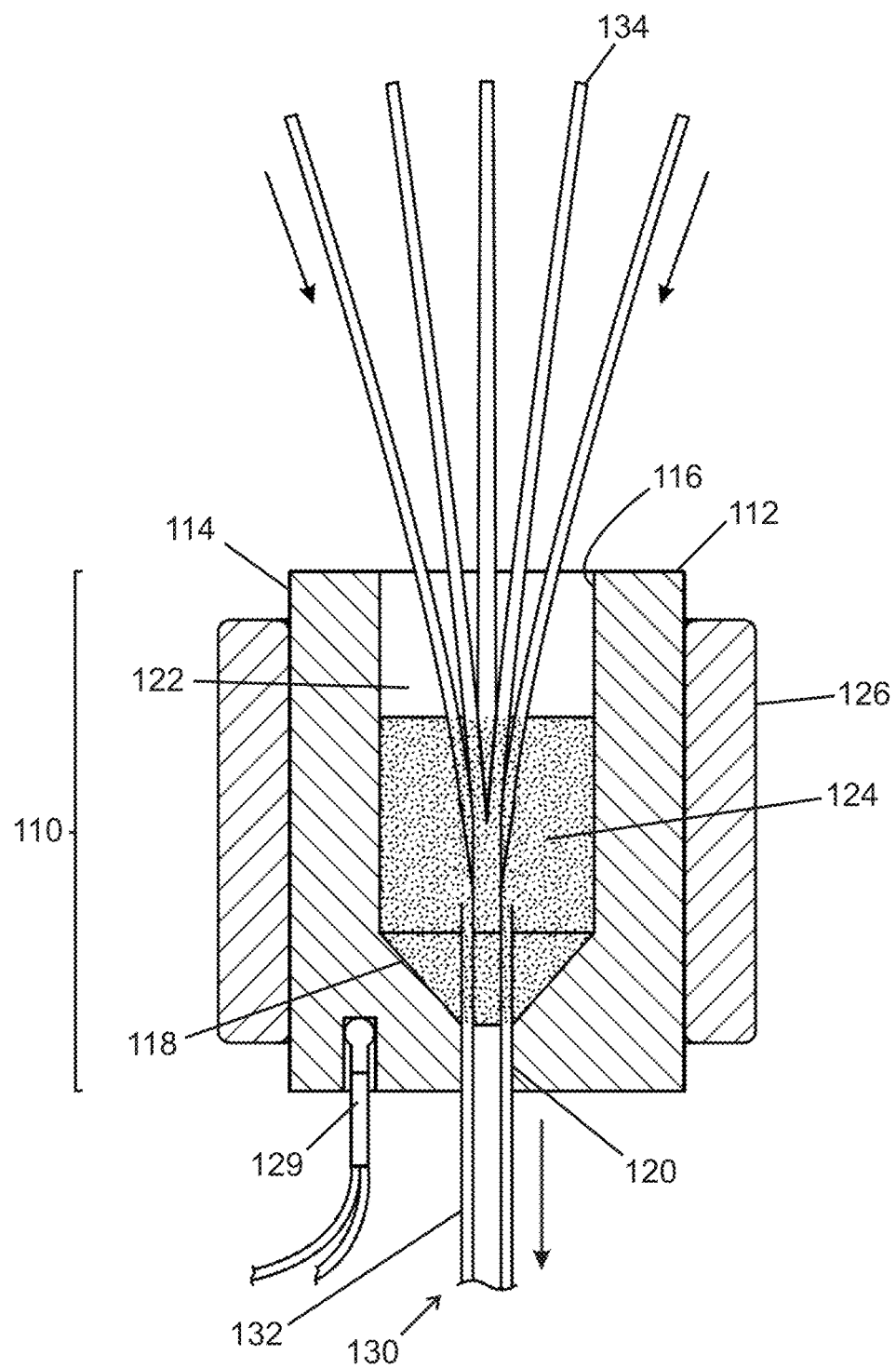
FIG. 6 is a schematic cross-sectional view of a die portion of the pultruder of FIG. 5.

FIG. 5 depicts a pultruder 100 used to make prototypes of bundled wire systems according to the prototype designs A to E described hereinabove. The pultruder 100 includes a support rod 102 and an adjustable height linkage 104 with a shelf 106 that supports a heated die portion 110, with a clamp 108 affixing a die 112 to the shelf 106. The pultruder 100 is configured to receive wires 134 from above, contain molten material therein, and eject a cylindrical wire bundle at bottom. FIG. 6 is a schematic cross-sectional view of the heated die portion 110 of the pultruder 100 of FIG. 5. Referring to FIG. 6, the heated die portion 110 includes the die 112, which is fabricated of aluminum and has a substantially cylindrical outer wall 114 surrounded at least in part by a peripheral heating collar 126 that is configured to supply heat to the die 112. The die 112 further includes a cavity 122 bounded by an upper or entrance opening 116, a tapered lower wall 118, and a lower or exit opening 120. In use, straight wires 134 are fed through the upper or entrance opening 116 and into the cavity 122 of the die 112 to contact molten PCL 124 contained therein. Feedback control of temperature is provided with a thermocouple 129 in conductive communication with the die 112. When the wires 134 are fed into the die 112, molten PCL 124 coats the wires 134 externally and therebetween, and as the wires 134 are pulled through the lower or exit opening 120, the wires 134 and solidified PCL 132 form a cylindrical bundle 130 having the same diameter as the lower or exit opening 120. Specifically, the close fit of the lower or exit opening 120 packs the wires 134 together into the cylindrical bundle 130, which is held together by solidified PCL 132 (i.e., that solidifies from molten PCL 124 as it cools).

Figure 7A:
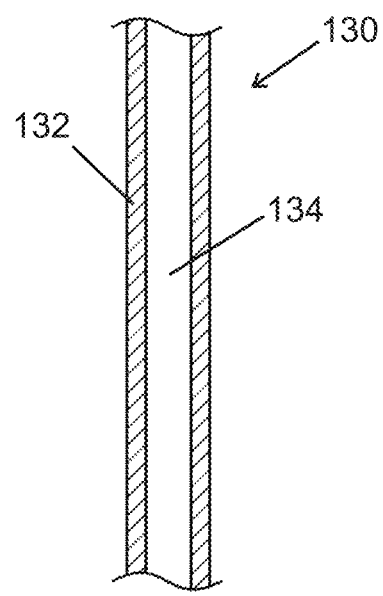
FIG. 7A is a schematic cross-sectional view of a section of an exemplary bundled wire system including a biocompatible adhesive polymer arranged between and around multiple wires.
Figure 7B:
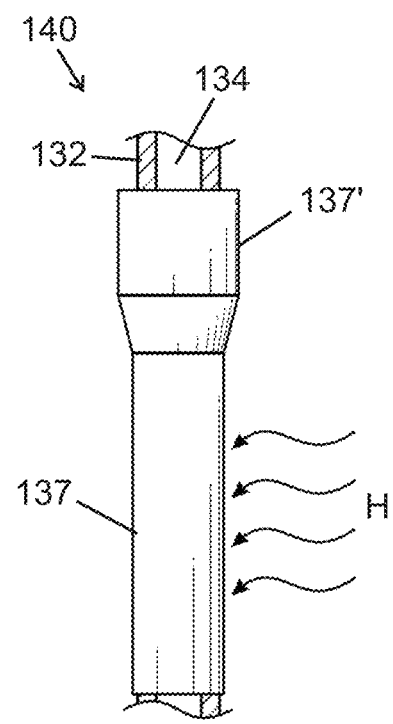
FIG. 7B is a schematic elevation view of a section of another exemplary bundled wire system similar to the bundled wire system of FIG. 7A, following application of a polyolefin coating around a subassembly of wires and polycaprolactone (PCL) upon exit from a pultruder.
Figure 7C:
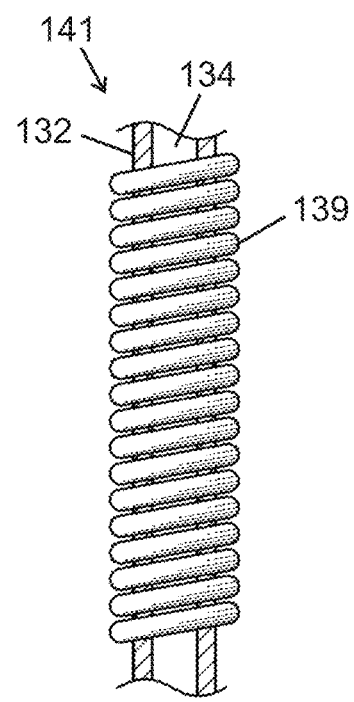
FIG. 7C is a schematic elevation view of a section of another exemplary bundled wire system similar to the bundled wire system of FIG. 7A, in which wires and PCL are pushed through a coil spring while the wires and PCL are still warm.

Three different bundled wire system configurations obtainable at least in part using the pultruder 100 and heated die portion 110 illustrated in FIGS. 5 and 6 are schematically illustrated in FIGS. 7A to 7C. FIG. 7A illustrates an exemplary bundled wire system 130 obtained by feeding multiple wires 134 through a pultruder 100 and permitting PCL 132 to cool around and between the wires 134. FIG. 7B illustrates an exemplary bundled wire system 140 similar to the bundled wire system 130 of FIG. 7A, but following application of a polyolefin coating 137 (e.g., in the form of heat shrink tubing) around an exterior of PCL 132 and wires 134 upon exit from a pultruder (not shown). More specifically, a section of tubing 137' may receive heat H from a heat source (not shown) to cause the tubing 137' to contract and form the polyolefin coating 137. FIG. 7C illustrates an exemplary bundled wire system 141 similar to the bundled wire system 130 of FIG. 7A, wherein the wires 134 and PCL 132 exiting a pultruder (not shown) are pushed through a coil spring 139 while the wires 134 and PCL 132 are still warm.

Figure 8A:
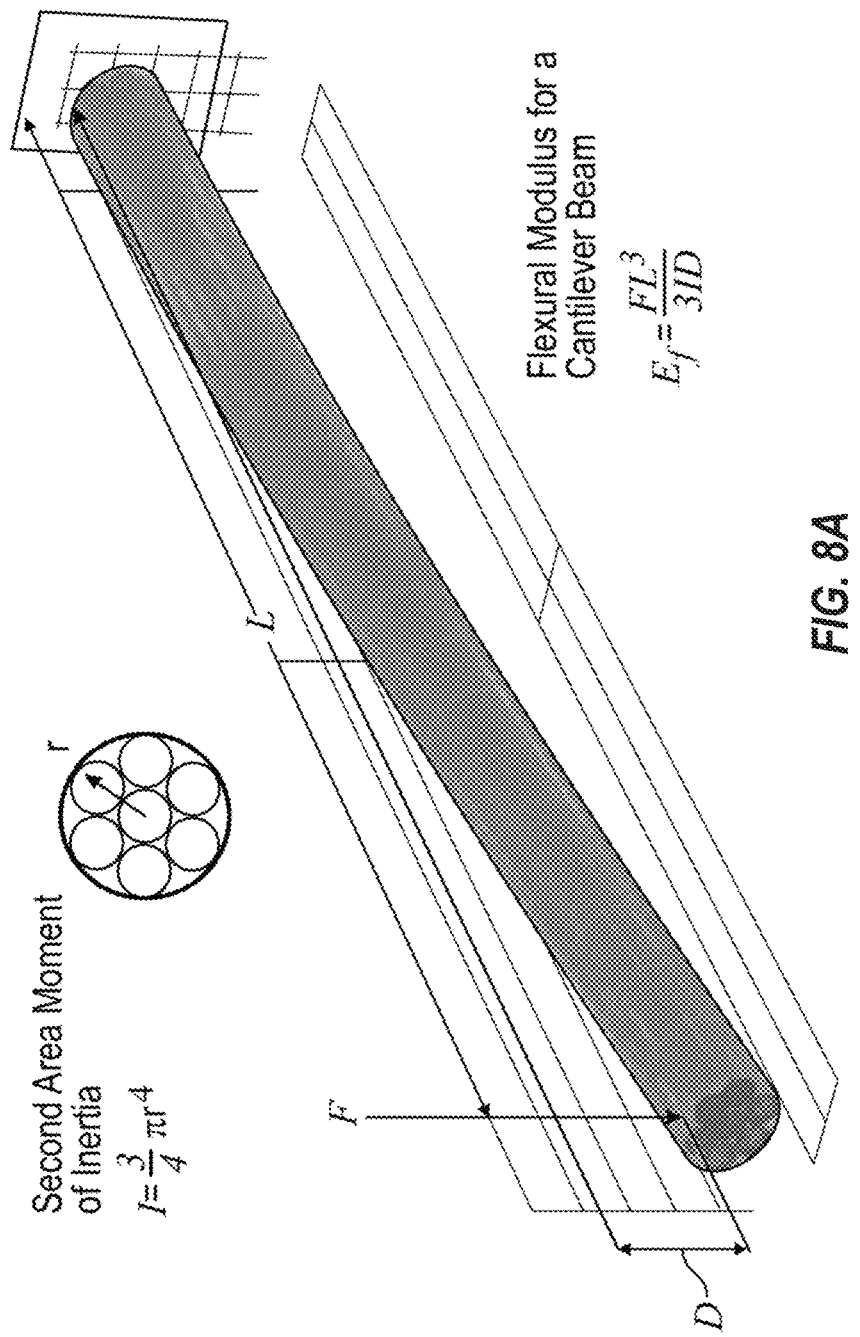
FIG. 8A is a perspective view of a modeling diagram of the bundled wire system according to prototype design A described in connection with FIG. 4, to permit finite element analysis (FEA) of the bundled wire system as a cantilever beam subject to bending.
Figure 8B:
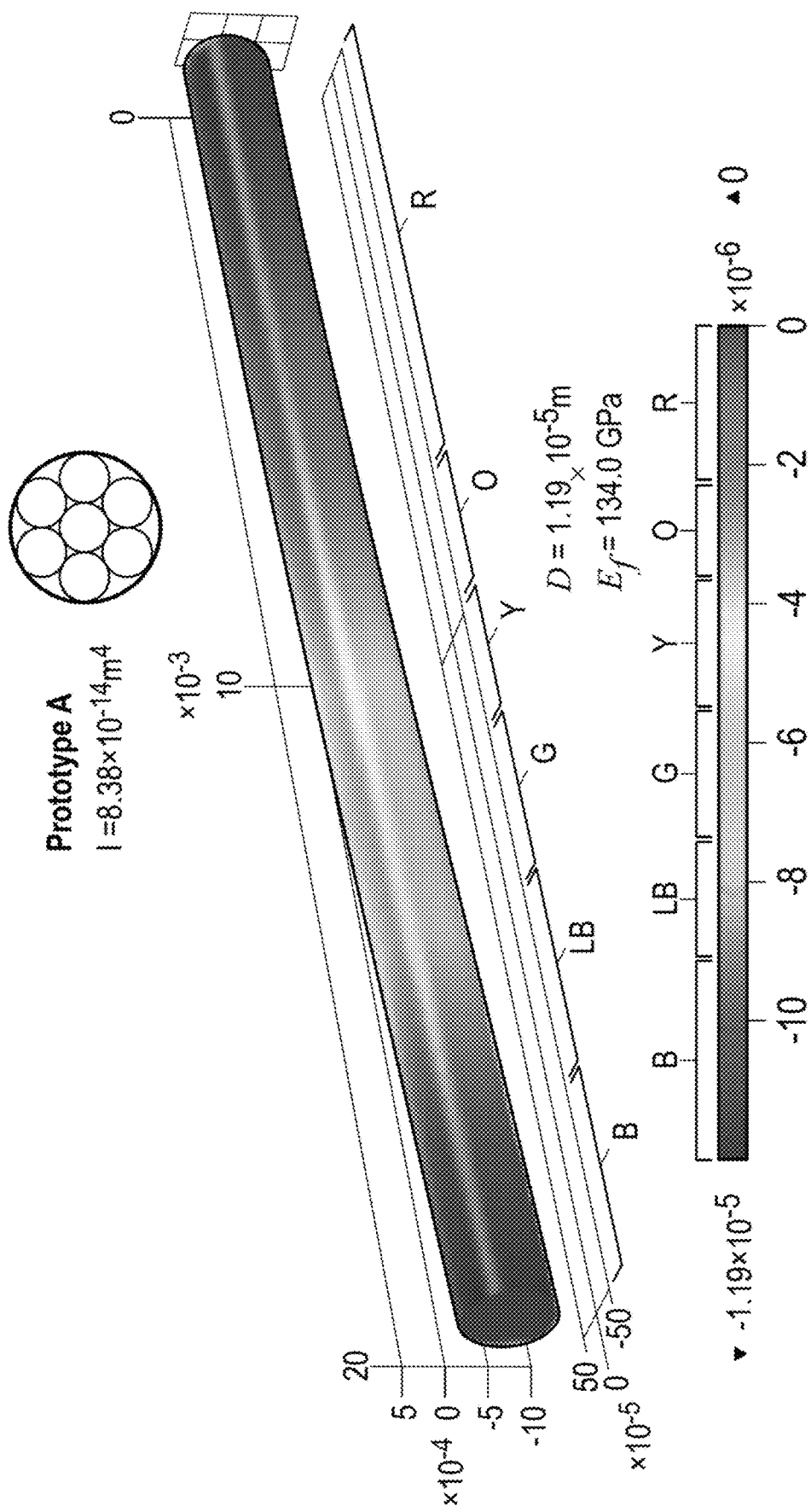
FIG. 8B provides graphical FEA modeling results for the bundled wire system according to prototype design A of FIG. 8A in the stiff (cool) state.
Figure 8C:
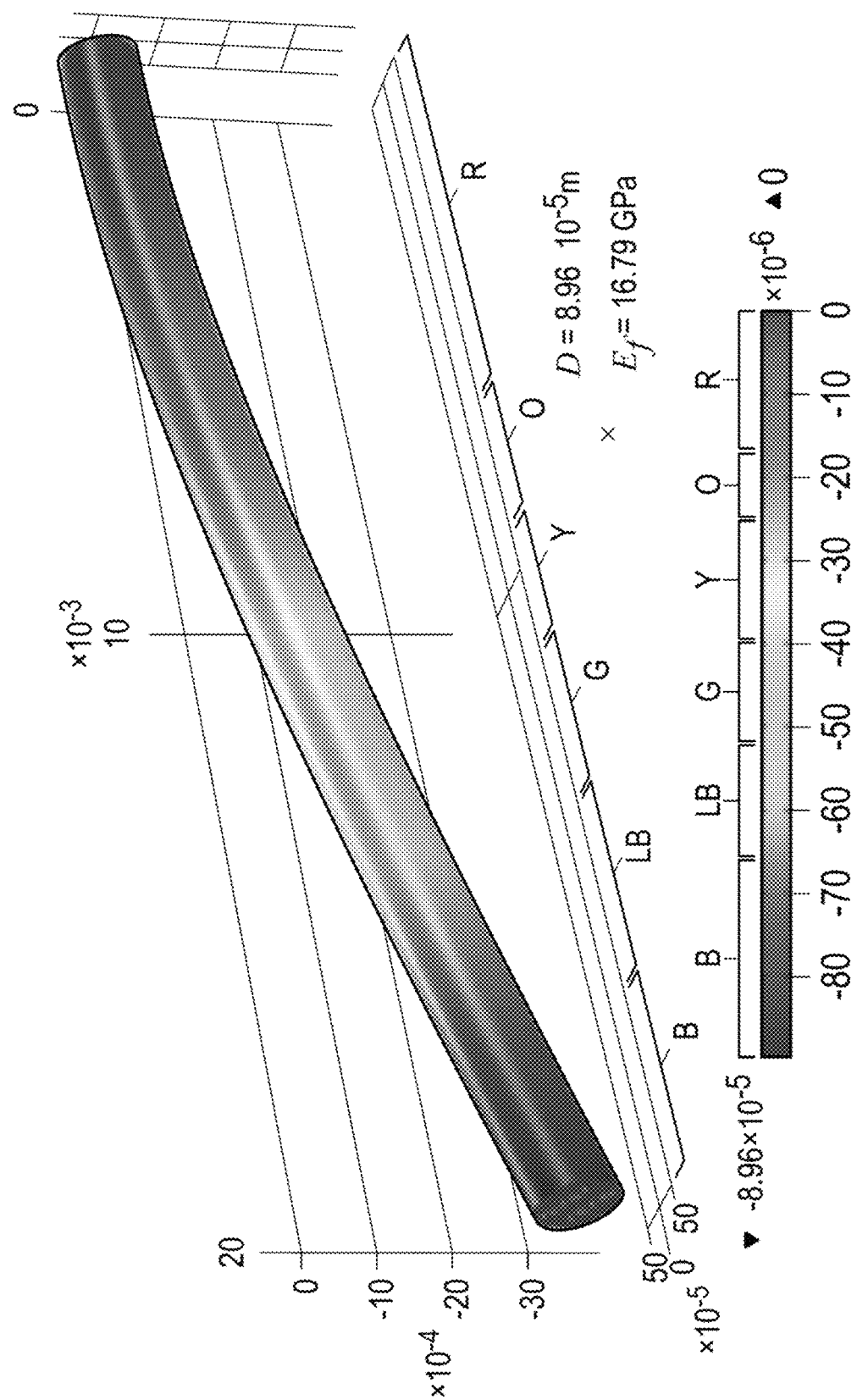
FIG. 8C provides graphical FEA modeling results for the bundled wire system according to prototype design A of FIG. 8A in the floppy (warm) state.

Examples of the above-described five different bundled wire systems 50, 60, 70, 80, 90 according to prototype designs A to E were subjected to finite element analysis (FEA) modeling to provide predicted performance as well as physical analysis to yield measured performance. FIG. 8A is a perspective view modeling diagram of the bundled wire system 50 according to prototype design A, following finite element analysis as a cantilever beam subject to bending (with one end fixed and the other end free). A beam length of 0.02 meters and an applied load of 0.05 Newtons were used, with the model being used to measure displacement D of the free end under application of an edge load F to determine flexural modulus in stiff and floppy states, to permit calculation of flexural modulus (equal to the product of the edge load F times the length of the beam L cubed, divided by three times the product of the second area moment of inertia and the displacement). FIG. 8B provides graphical FEA modeling results (including deformation as a function of position) for the bundled wire system 50 according to prototype design A in the stiff (cool) state, and FIG. 8C provides graphical FEA modeling results for the bundled wire system 50 according to prototype design A in the floppy (warm) state. FIGS. 8B and 8C embody diagrams converted from color to grayscale, and in each figure, letter codes have been added to the figure and corresponding legend to permit visualization of flexural modulus values as follows: R=red, O=orange, Y=yellow, G=green, LB=light blue, and B=blue. The modulus of elasticity $E_f$ was reduced from 134 GPa in the stiff (cool) state (shown in FIG. 8B) to less than 17 GPa in the floppy (warm) state (shown in FIG. 8C).

FIG. 9A illustrates an INSTRON® materials testing machine 150 (Illinois Tool Works Inc., Glenview, Ill., US), and FIG. 9B illustrates a magnified portion of the same machine 150, used to apply three point bending to physical samples using an upper cylindrical roller 151 configured to translate downward and apply a force F along a centerline between two lower cylindrical rollers 152, 153 spaced apart by a distance L. In one set of tests, the force F required to attain a displacement D was measured in order to determine the flexural modulus $E_f$ of a prototype bundled wire system, with determination of F and D when the prototype fails. A length L of 0.04 meter between the lower cylindrical rollers 152, 153 was used. The flexural modulus for a beam subjected to three-point bending is calculated as the applied force times the length cubed, divided by forty-eight times the product of the second area moment of inertia and the diameter. Each prototype bundled wire system 50, 60, 70, 80, 90 according to prototype designs A to E was tested in a stiff state (cool, with no electric current) and a floppy state (in which electric current was applied to the core wires to heat the sample). Another protocol using the same INSTRON® materials testing machine 150 was used to perform a deformation-holding test on each prototype bundled wire system 50, 60, 70, 80, 90, with the deformation-holding test serving to measure the extent to which the bundled wire system 50, 60, 70, 80, 90 held its deformed shape (and therefore resisted straightening due to internal stresses of bent wires) after cooling. The idea is to determine the minimum bending radius that the thermoplastic adhesive can sustain without failing. In each case, a prototype bundled wire system 50, 60, 70, 80, 90 was subjected to three-point bending, whereby the bundled wire system was bent to a prescribed displacement when in the floppy (warm) state, then allowed to cool while displaced/loaded, followed by removal of the load. Thereafter, the displacement to which the bundled wire system springs back was measured, and scrutiny was applied to observe any adhesion failure. The minimum radius of curvature for any given displacement D at the midpoint is calculated as the length squared divided by twelve times the displacement D.

Figure 10:
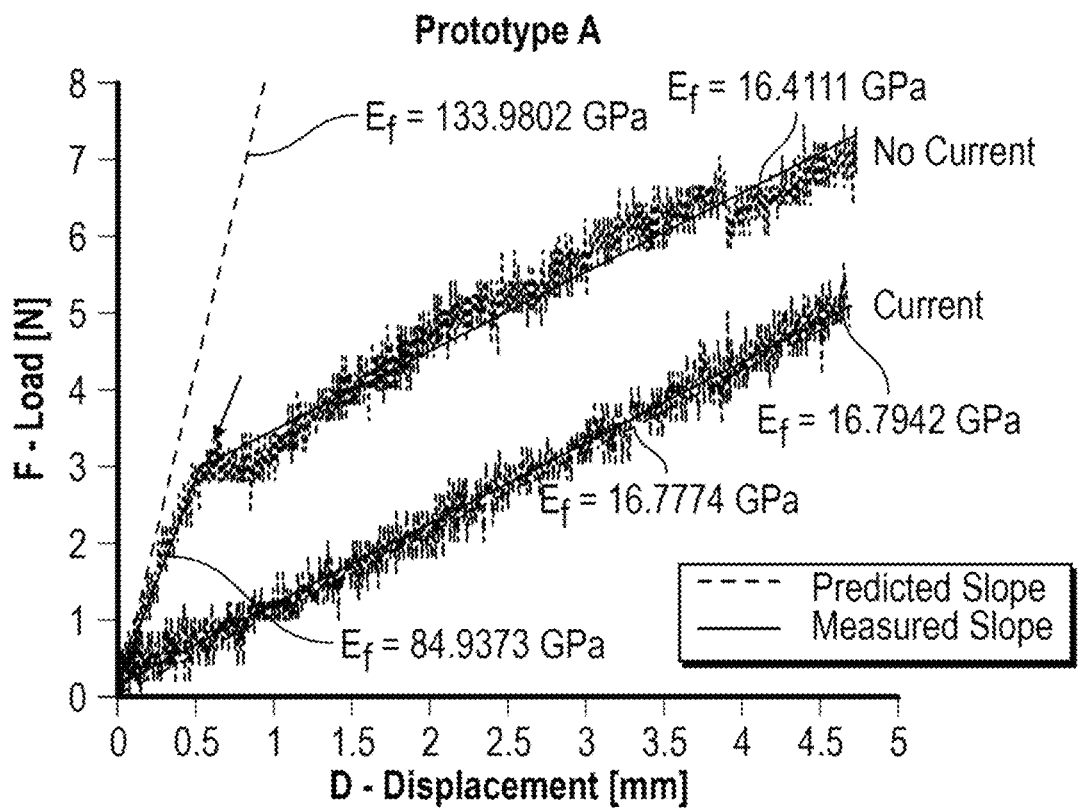
FIG. 10 is a plot of load or force versus displacement for "no current" (corresponding to a stiff or cool state) and "current" (corresponding to a floppy or warm state) conditions, including predicted slope obtained by FEA modeling and measured slope obtained by empirical testing for the bundled wire system according to prototype design A, including seven wires and adhesive without any coating, as described in connection with FIG. 4.
Figure 11:
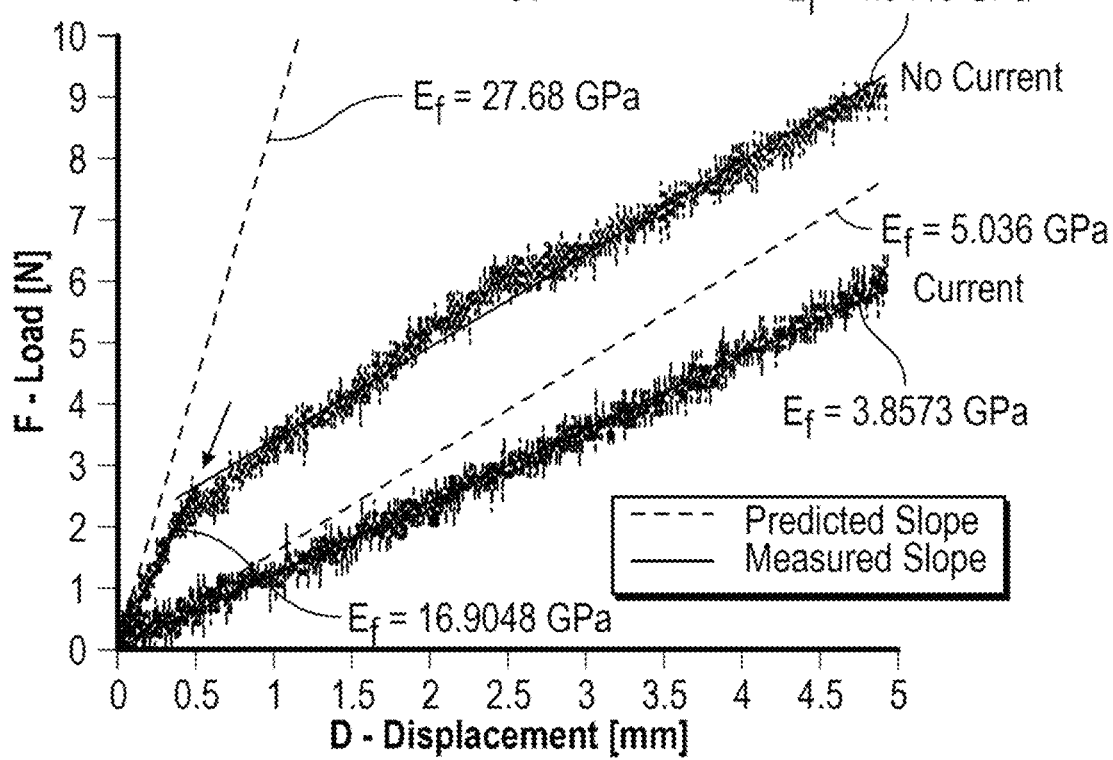
FIG. 11 is a plot of load or force versus displacement for "no current" (corresponding to a stiff or cool state) and "current" (corresponding to a floppy or warm state) conditions, including predicted slope obtained by FEA modeling and measured slope obtained by empirical testing for the bundled wire system according to prototype design B, including seven wires and adhesive sheathed in polyolefin heat shrink tubing, as described in connection with FIG. 4.
Figure 12:
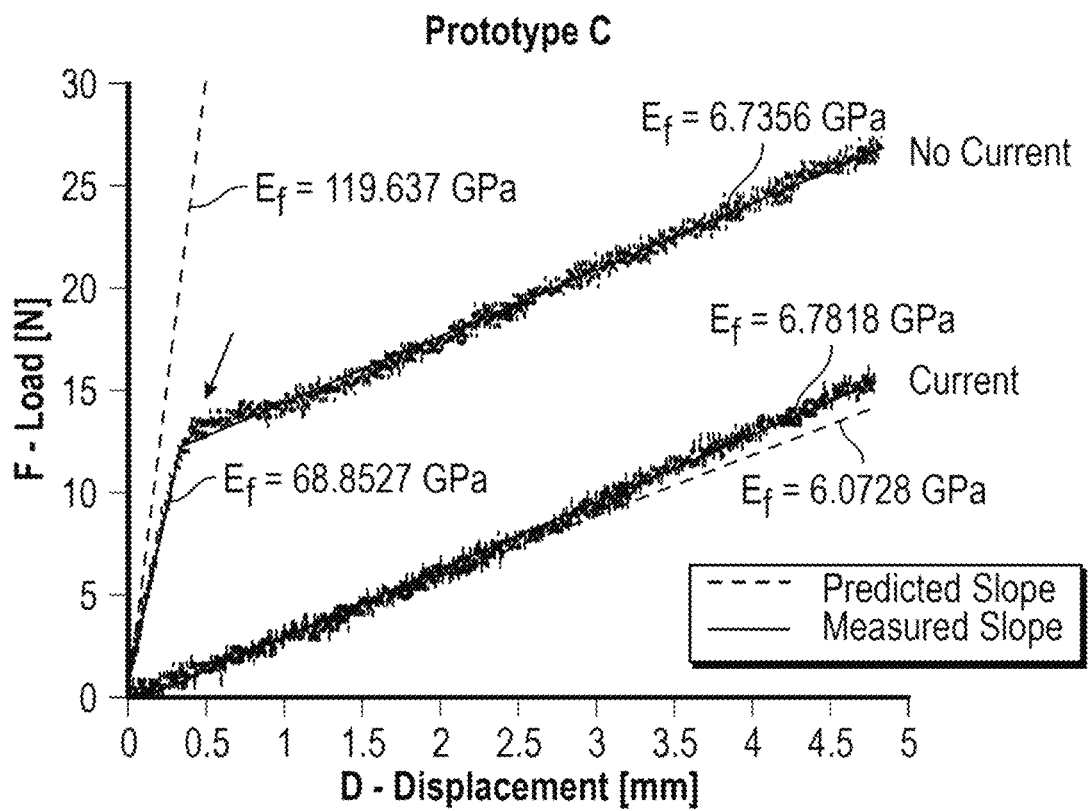
FIG. 12 is a plot of load or force versus displacement for "no current" (corresponding to a stiff or cool state) and "current" (corresponding to a floppy or warm state) conditions, including predicted slope obtained by FEA modeling and measured slope obtained by empirical testing for the bundled wire system according to prototype design C, including nineteen wires and adhesive without any coating, as described in connection with FIG. 4.
Figure 13:
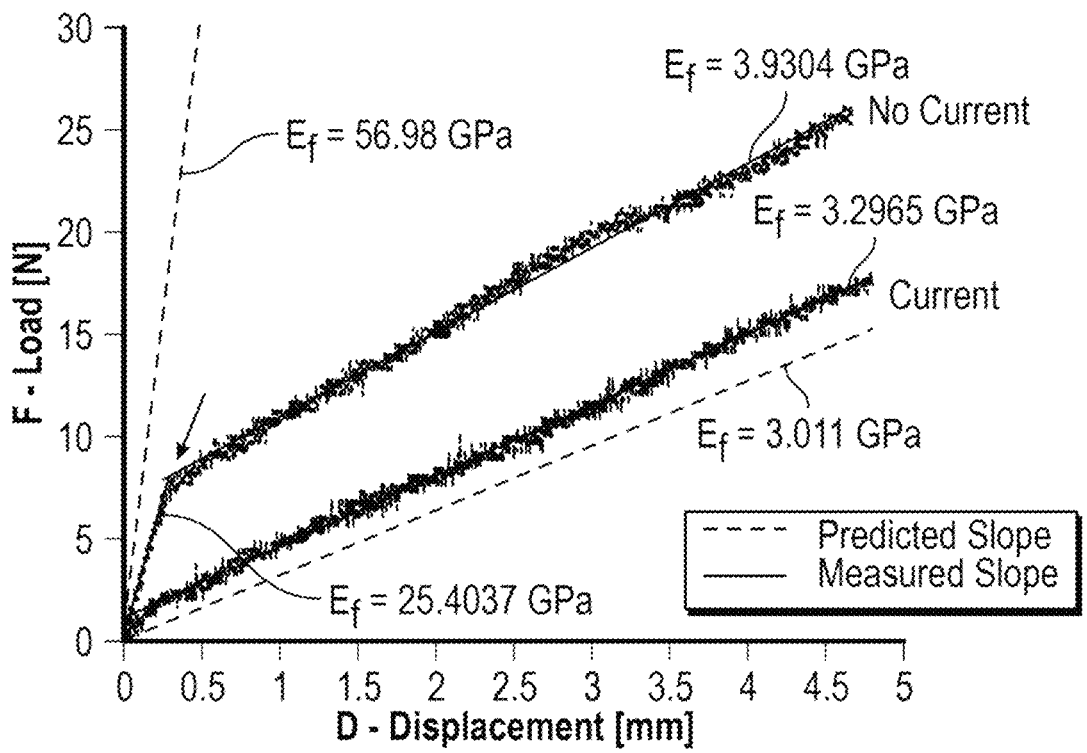
FIG. 13 is a plot of load or force versus displacement for "no current" (corresponding to a stiff or cool state) and "current" (corresponding to a floppy or warm state) conditions, including predicted slope obtained by FEA modeling and measured slope obtained by empirical testing for the bundled wire system according to prototype design D, including nineteen wires and adhesive sheathed in polyolefin heat shrink tubing, as described in connection with FIG. 4.
Figure 14:
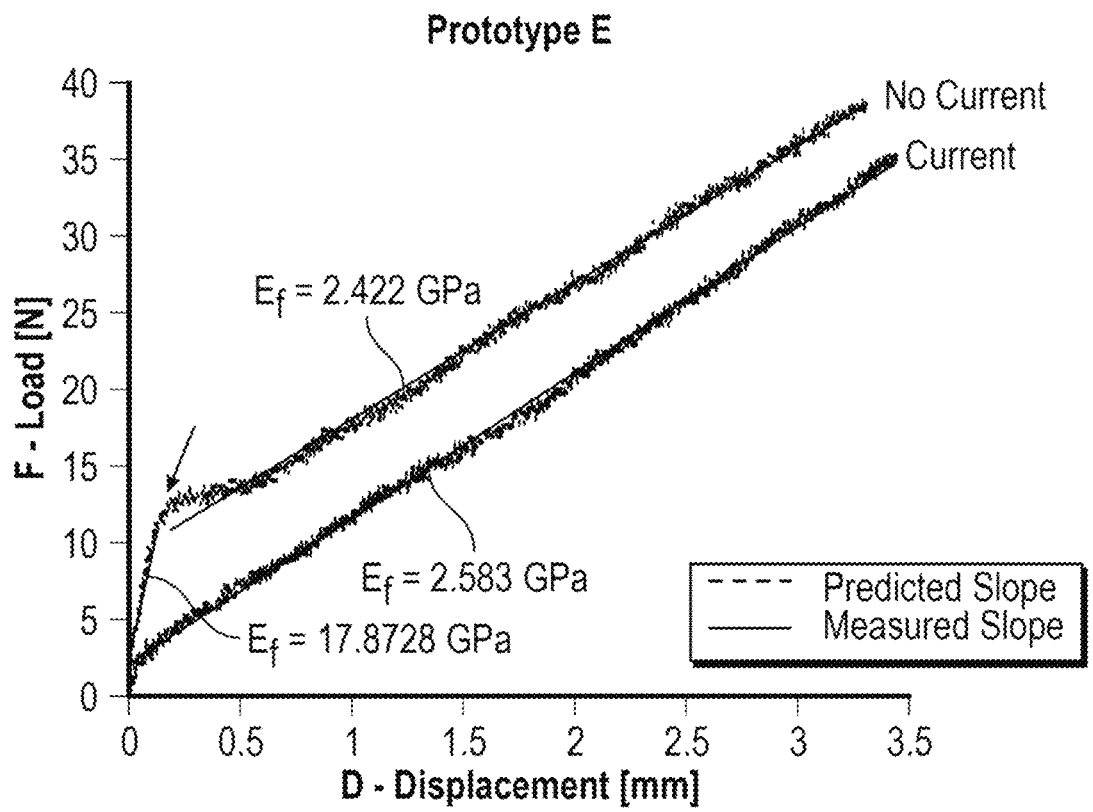
FIG. 14 is a plot of load or force versus displacement for "no current" (corresponding to a stiff or cool state) and "current" (corresponding to a floppy or warm state) conditions, including predicted slope obtained by FEA modeling and measured slope obtained by empirical testing for the bundled wire system according to prototype design E, including nineteen wires and adhesive sheathed in a stainless steel spring, as described in connection with FIG. 4.

FIGS. 10-14 are plots of load or force F (in Newtons) versus displacement D (in millimeters), for "no current" (corresponding to a stiff or cool state) and "current" (corresponding to a floppy or warm state) conditions, including predicted slope obtained by FEA modeling and measured slope obtained by empirical testing (with an INSTRON® materials testing machine as outlined above), for the bundled wire systems 50, 60, 70, 80, 90 according to prototype designs A to E (illustrated and described in connection with FIG. 4), respectively. The slope of each line corresponds to flexural modulus $E_f$. FIG. 10 provides results for the bundled wire system 50 according to Prototype design A including seven wires and adhesive without any coating. Adhesion among wires in the bundled wire system 50 failed at around 0.48 mm at a force of approximately 2.8 N (indicated by the arrow at left). FIG. 11 provides results for the bundled wire system 60 according to Prototype B, including seven wires and adhesive sheathed in polyolefin heat shrink tubing. Adhesion among wires in the bundled wire system 60 failed at around 0.37 mm at a force of approximately 2.0 N (indicated by the arrow at left). FIG. 12 provides results for the bundled wire system 70 according to Prototype C, including nineteen wires and adhesive without any coating. Adhesion among wires in the bundled wire system 70 failed at around 0.435 mm at a force of approximately 13.2 N (indicated by the arrow at left). FIG. 13 provides results for the bundled wire system 80 according to Prototype D including nineteen wires and adhesive sheathed in polyolefin heat shrink tubing. Adhesion among wires in the bundled wire system 80 failed at around 0.28 mm at a force of approximately 7.2 N (indicated by the arrow at left). FIG. 14 provides results for the bundled wire system 90 according to Prototype E including nineteen wires and adhesive sheathed in a 0.125 inch (3.18 mm) stainless steel spring. Adhesion among wires in the bundled wire system 90 failed at around 0.15 mm at a force of approximately 11.2 N (indicated by the arrow at left).

In each of FIGS. 10-14, the "no current" or stiff (cool) state provides a substantially greater flexural modulus $E_f$ value than the "current" or floppy (warm) state. Upon review of FIGS. 10-14, it is apparent that the "cool" wire bundles exhibit two slopes, including a high stiffness region characterized by a steep slope for up to about 0.5 mm until adhesion suddenly fails, and a low stiffness region characterized by a shallow slope in which stiffness is roughly equivalent to the "warm" or floppy state. Observation and inspection of the wires during and after this sudden change in slope showed that the wires and polymer adhesive indeed separated. Neither the polyolefin heat shrink tubing nor the stainless steel spring appeared to prevent or delay the onset of delamination; however, the stainless steel spring did keep the bundled wire system's circular cross-sectional shape from deforming, in contrast to all of the other prototypes A to D, which exhibited a flattened cross-section at the point where load was applied. All tested wires held their deformed shape when cooled from the warm state while held in position under load, and this could be reversed by reheating the wire electrically. There was a limit to how much bend a wire could hold without breaking the adhesion, and each wire exhibited a tendency to spring back. Each bundled wire system prototype would not straighten more when allowed to cool.

Figure 15:
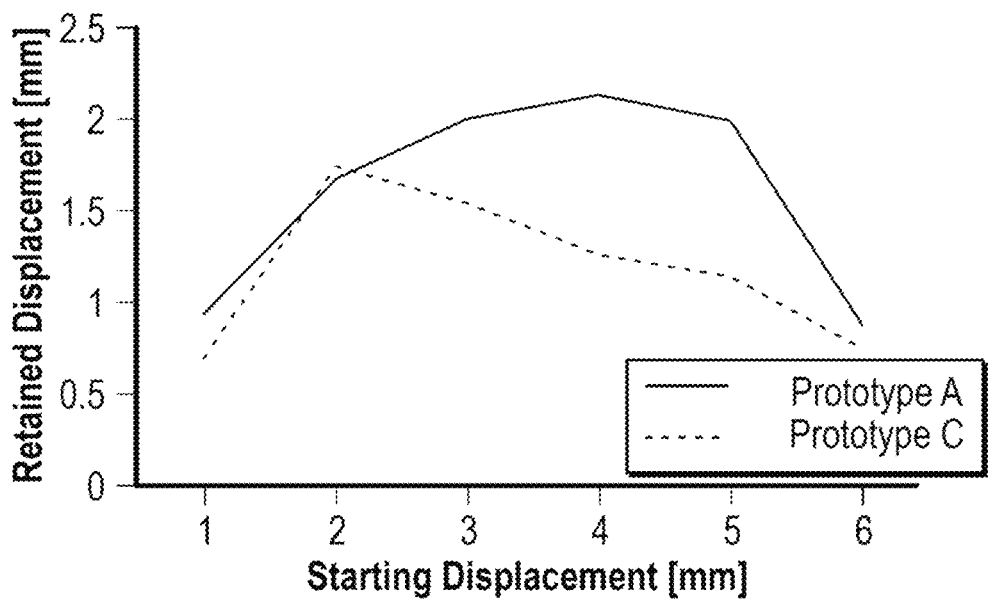
FIG. 15 is a plot of retained displacement (mm) versus starting displacement (mm) for bundled wire systems according to prototype designs A and C as described in connection with FIG. 4.

FIG. 15 is a plot of retained displacement (mm) versus starting displacement (mm) for bundled wire systems 50, 70 according to prototype designs A and C, and FIG. 16 is a table providing numerical results for the same bundled wire systems 50, 70 according to prototype designs A and C, obtained by the deformation-holding test described hereinabove. As shown in FIGS. 15 and 16, the bundled wire system prototypes 50, 70 can maintain some of the deformation/curvature they have undergone when cooled, up to a certain displacement. The solidified polymer adhesive resists some but not all of the straightening of the steel wires. Past this displacement, the bundled wire system prototypes 50, 70 lose the ability to maintain deformation/curvature in the cold state due to adhesion failure. In particular, the polymer adhesive peels from the metal, and the adhesion strength is not sufficient to resist the straightening of the wires without breaking.

FIG. 17 is a table summarizing numerical results of FEA modeled $E_f$ (stiff state), tested (physical) $E_f$ (stiff state), FEA modeled $E_f$ (floppy state), tested (physical) $E_f$ (floppy state), stiff state displacement at adhesion failure, stiff state radius of curvature at adhesion failure, force at stiff state adhesion failure, and minimum radius of curvature for bundled wire systems 50, 60, 70, 80, 90 according to prototype designs A to E (illustrated and described in connection with FIG. 4). In general, the FEA models appear to accurately predict $E_f$ values of the prototypes A to E in the floppy state, thereby suggesting that in the floppy state, each bundled wire system prototype 50, 60, 70, 80, 90 behaves as a bundle of uncoupled wires. However, the FEA models generally overestimate $E_f$ values for the bundled wire system prototypes 50, 60, 70, 80, 90 in the stiff state. This may suggest that the effective $E_f$ value of the polymer adhesive is less than the literature value used in the FEA model, and/or it may suggest the possible existence of voids between the wires in which polymer adhesive is absent, thereby decreasing adhesion strength and lowering the effective stiffness of the PCL between the wires.

FIG. 18 is a table summarizing numerical results of flexural modulus and minimum radius of curvature without plastic deformation, as well as observations as to whether shape is maintained during stiffness change, for bundled wire systems 50, 70 according to prototype designs A and C.

The preceding disclosure including FIGS. 3 to 18 demonstrates the viability of bundled wire systems as prototypes for guidewires having stiffness properties that can be changed by coupling at least one electrical conductor (e.g., one or more bundled wire systems) with an electric power source for resistive heating of a polymer adhesive binding the wires, by which a stiffness property of the polymer adhesive may be adjusted. Although adhesion between wires was not necessarily improved by external application of polyolefin coatings or helical coil springs, the use of coil springs did preserve the circular cross-section of a wire bundle, which would tend to permit advancement of a catheter utilizing a bundled wire system (as opposed to potential jamming of a catheter during advancement over a guidewire if a bundle of wires were flattened in shape). Wires within a bundle tend to straighten in a cool state, but, unlike moveable core wires of a conventional moveable guidewire, a bundled wire system guidewire as described in connection with the foregoing figures would not apply more straightening force against vessel walls when stiffness is increased.

Consistent with the foregoing disclosure, in one aspect, the present disclosure relates to a guidewire device including a tube having a longitudinal axis, a first end, a second end, and an interior; and including a plurality of wires arranged in or on the tube; wherein the tube comprises a polymer adhesive, and at least one wire of the plurality of wires is configured to be coupled with an electric power source for resistive heating of the polymer adhesive to adjust a stiffness property of the polymer adhesive. In certain embodiments, at least some wires of the plurality of wires include metal. In certain embodiments, at least some wires of the plurality of wires include conductive polymer material or composite material. In certain embodiments, combinations of wires including metal and wires including conductive polymer and/or composite materials may be used.

Figure 19:
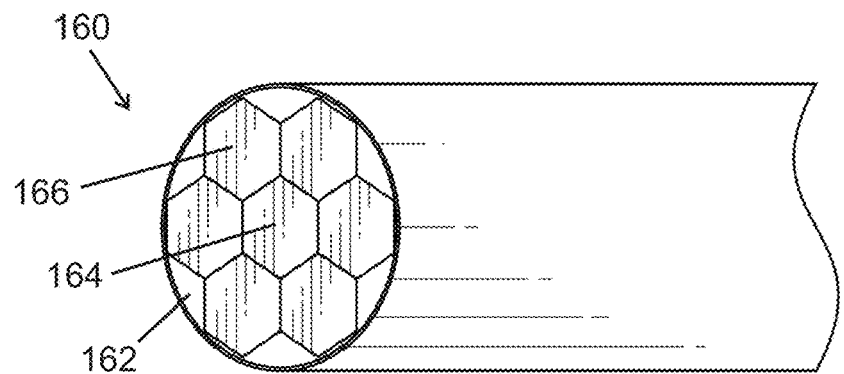
FIG. 19 illustrates a bundled wire system including six wires each having a hexagonal cross-sectional shape bundled around a central wire also having the same shape, with polymer adhesive arranged around and between the wires and forming a generally tubular shape.
Figure 20:
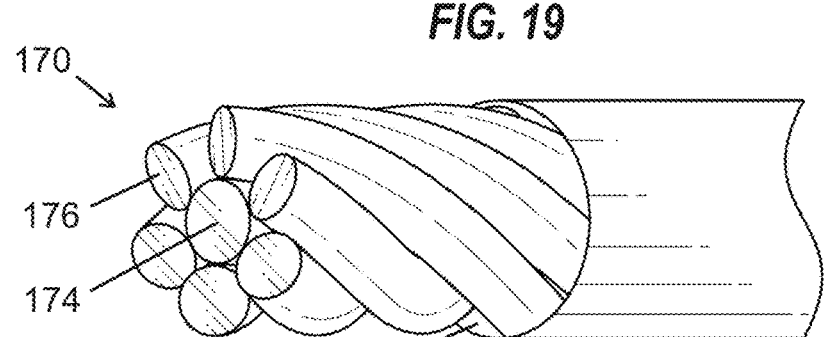
FIG. 20 illustrates a bundled wire system in which multiple wires of round cross-sectional shapes are twisted about a central core wire, with polymer adhesive preferably arranged around and between the wires.

To address certain issues experienced with use of bundled wire system guidewire prototypes including parallel wires of round cross-sectional shapes, other wire shapes and/or orientations may be used. For example, FIG. 19 illustrates a bundled wire system 160 including six wires 166 each having a hexagonal cross-sectional shape bundled around a central wire 164 also having the same shape, with polymer adhesive 162 arranged around and between the wires 164, 166 and forming a generally tubular shape. More generally, in certain embodiments, each wire of a plurality of wires may include a polygonal cross-sectional shape, or may include at least one flat side surface (preferably multiple flat side surfaces) arranged to contact a flat side surface of another adjacent wire. As another example, FIG. 20 illustrates a bundled wire system 170 in which multiple (e.g., six) wires 176 of round cross-sectional shapes are twisted about a central core wire 174, with polymer adhesive 172 preferably arranged around and between the wires 174, 176. Alternatively, multiple wires may be braided. The preceding conformations may assist in maintaining wires in a generally round bundle even when a polymer adhesive contacting the wires is in a softened (e.g., warm and "floppy") state.

Figure 21:
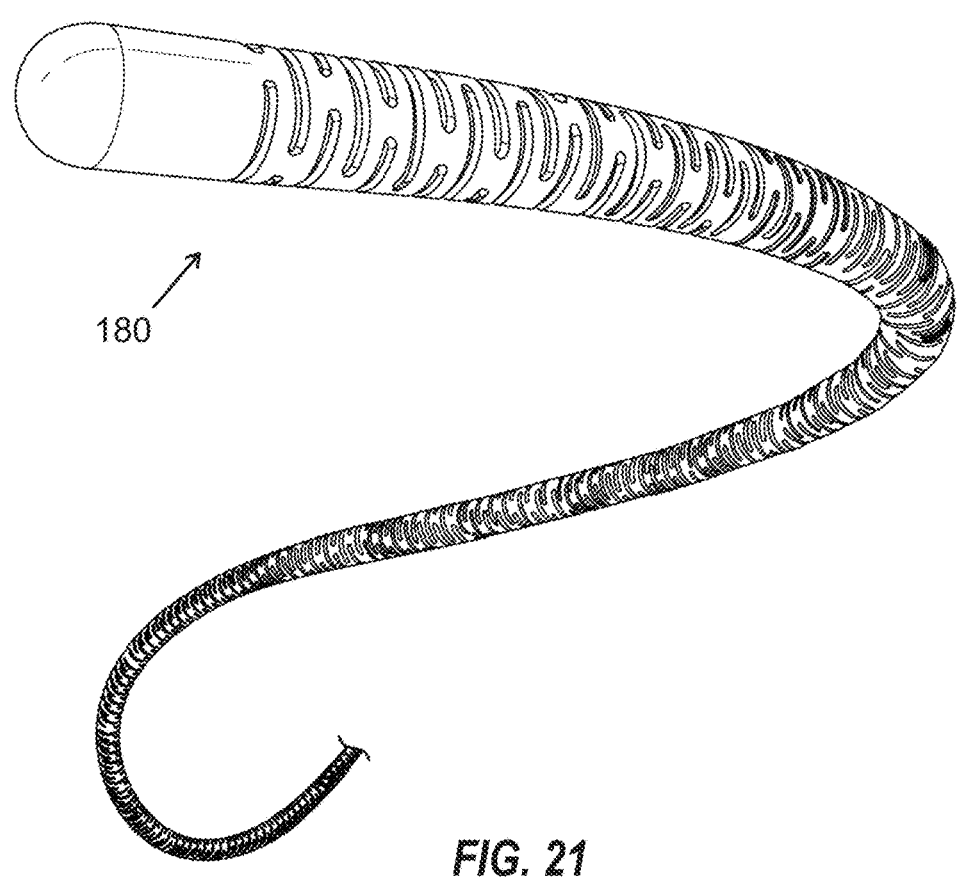
FIG. 21 illustrates an external sheath of a commercially available JOURNEY® guidewire.

In certain embodiments, guidewire devices as disclosed herein may include a metal coil spring extending generally parallel to a longitudinal axis of a tube or tubular body, and surrounding at least a portion of the tube or tubular body. In other embodiments, guidewire devices as disclosed herein may include a flexible metal sheath extending generally parallel to a longitudinal axis of a tube or tubular body, and surrounding at least a portion of the tube or tubular body. Such a coil spring or flexible metal sheath may embody an outer surface of a guidewire. One example of a flexible metal sheath 180 is shown in FIG. 21, which depicts an external sheath of a JOURNEY® guidewire (Boston Scientific Scimed, Inc., Maple Grove, Minn., US). In certain embodiments, a metal coil spring or flexible metal sheath may be used in lieu of a wire bundle within a tube, with the potential of providing improved bidirectional torque transmission.

FIG. 22A schematically illustrates a portion of a guidewire device 190 in which stiffness at one or more locations may be adjusted by selective operation or modulation of one or more electromagnetic elements. The guidewire device 190 includes a tubular body (e.g., a tube) 191 including multiple variable stiffness segments 192A, 192B that may be separated by segments 199 lacking variable stiffness capability. In each variable stiffness segment 192A, 192B, a compressible and/or extensible material 193A, 193B is arranged between an electromagnet 194A, 194B and at least one magnetically responsive element 197A, 197B. The electromagnet 194A, 194B is configured to receive at least one electrical signal to selectively generate a magnetic field sufficient to interact with the at least one magnetically responsive element 197A, 197B, thereby exerting a compression or extension force on the compressible and/or extensible material 193A, 193B to adjust a stiffness of the variable stiffness segment 192A, 192B. In certain embodiments, when an electromagnet 194A, 194B is energized to exert an attractive force on at least one magnetically responsive element 197A, 197B (e.g., a metal such as carbon steel) separated therefrom by a compressible and/or extensible material 193A, 193B, the resulting attraction (as indicated by the vertically arranged arrows shown in FIG. 22A) tends to compress the compressible and/or extensible material 193A, 193B, thereby increasing stiffness of the variable stiffness segment(s) 192A, 192B. In certain embodiments, when an electromagnet 194A, 194B is energized to exert a repelling force on at least one magnetically responsive element 197A, 197B (e.g., a magnet or another electromagnet of the same polarity), the resulting repulsion tends to elongate or extend the compressible and/or extensible material 193A, 193B, thereby decreasing stiffness of the variable stiffness segment(s) 192A, 192B.

FIG. 22B schematically illustrates a portion of another guidewire device 200 in which stiffness at one or more locations may be adjusted by selectively operation or modulation of one or more electromagnetic elements 204A, 204B. The guidewire device 200 includes a tubular body (e.g., a tube) 201 including multiple variable stiffness segments 202A, 202B, with longitudinally extending conductors 208-1, 208-2 inset slightly relative to the tubular body 201. In each variable stiffness segment 202A, 202B, a compressible and/or extensible material 203A, 203B is arranged between an electromagnetic element 204A, 204B and at least one magnetically responsive element 207A, 207B. Each electromagnetic element 204A, 204B includes contact regions 205A, 205B, 206A, 206B arranged for conductive electrical communication with the longitudinally extending conductors 208-1, 208-2. In certain embodiments, one or more contact regions 205A, 205B, 206A, 206B may include switching or gating elements arranged to control flow of current through an electromagnetic element 204A, 204B. In certain embodiments, each variable stiffness segment 202A, 202B may include one or more dedicated electrical conductors and/or each variable stiffness segment 202A, 202B may be independently controlled. In certain embodiments, each variable stiffness segment 202A, 202B may be separated from one another by at least one segment 209 lacking variable stiffness capability.

With respect to FIGS. 22A and 22B, in certain embodiments, the compressible and/or extensible material 193A, 193B, 203A, 203B includes a foam material, which may embody a three-dimensional matrix. In certain embodiments, multiple variable stiffness segments 192A, 192B, 202A, 202B may be sequentially arranged along the longitudinal axis of a guidewire device 190, 200, and may be independently controlled. In certain embodiments, longitudinally extending conductors (e.g., 208-1, 208-2) may be arranged in or on the tubular body structure 191, 201 and operatively coupled with one or more variable stiffness segments 192A, 192B, 202A, 202B (e.g., including electromagnetic elements thereof) to supply electrical signals for adjusting stiffness. In certain embodiments, a tubular body 191, 201 may comprise a polymer adhesive, and a guidewire 190, 200 may include at least one electrical conductor configured to be coupled with an electric power source (not shown) for resistive heating of the polymer adhesive to adjust a stiffness property of the polymer adhesive. In certain embodiments, a plurality of circumferentially contractible fiber regions (e.g., piezoelectric material, an electroactive polymer, or a nitinol alloy, not shown but described hereinafter in connection with FIGS. 28A-30) may be arranged in or on the tubular body 191, 201, wherein each circumferentially contractible fiber region is longitudinally spaced from each other circumferentially contractible fiber region. In certain embodiments, a plurality of radially contractible fiber regions (not shown, but described hereinafter in connection with FIGS. 28A-30) may be arranged in or on the tubular body 191, 201, wherein each radially contractible fiber region (e.g., piezoelectric material, an electroactive polymer, or a nitinol alloy) is longitudinally spaced from each other radially contractible fiber region. If provided, each circumferentially contractible fiber region or radially contractible fiber region may further permit adjustment of stiffness and/or aid in steering in one or more regions of the guidewire element. In certain embodiments, a metal coil spring or flexible metal sheath (not shown, but described previously herein) may extend generally parallel to the longitudinal axis and surround at least a portion of the tubular body.

Figure 23A:
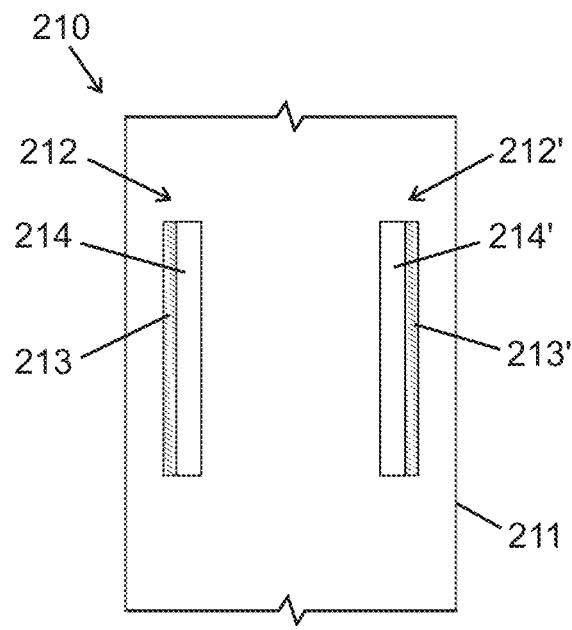
FIG. 23A is a schematic cross-sectional view of a portion of a guidewire device according to one embodiment in which angle or radius of curvature at one or more locations may be adjusted by applying current to electrically operable adjustable flexure elements arranged in or on a tubular body, in which each flexure element of a pair of adjustable flexure elements is in a straightened state.
Figure 23B:
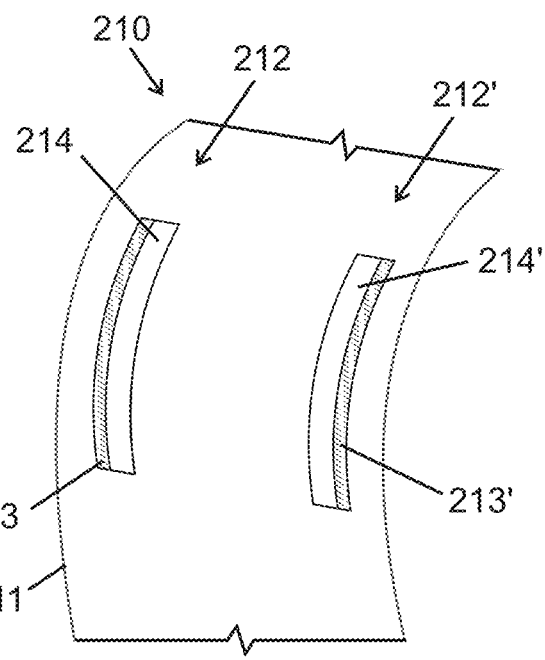
FIG. 23B is a schematic cross-sectional view of a portion of the guidewire device of FIG. 23A, in which the pair of adjustable flexure elements is curved to the left.
Figure 23C:
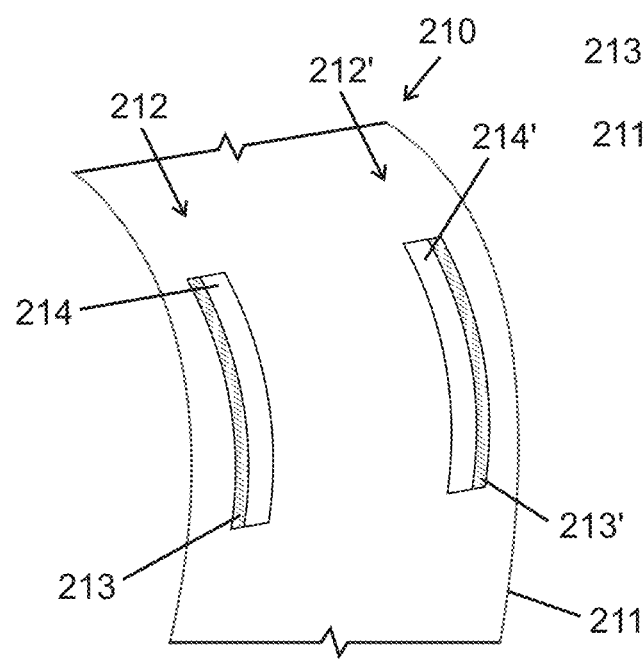
FIG. 23C is a schematic cross-sectional view of a portion of the guidewire device of FIG. 23A, in which the pair of adjustable flexure elements is curved to the right.

FIGS. 23A-23C provide schematic cross-sectional views of a portion of a guidewire device 210 in which angle or radius of curvature at one or more locations may be adjusted by applying current to electrically operable adjustable flexure elements 212, 212' arranged in or on a tubular body 211. FIGS. 23A-23C each illustrates a pair of adjustable flexure elements 212, 212' that are longitudinally oriented proximate to sides of the tubular body 211. Each adjustable flexure element 212, 212' may include a coating layer or backbone layer 213, 213' (e.g., a metal) arranged in contact with an electrically responsive material 214, 214' (e.g., a piezoelectric material, an electroactive polymer, or a nitinol alloy) that contracts, bends, or straightens with application of different voltage. The metal coating layer or backbone layer 213, 213' may be used to adjust rigidity or compliance of the adjustable flexure element 212, 212'. In certain embodiments, for each adjustable flexure element 212, 212', the electrically responsive material 214, 214' may be medially located, and the coating layer or backbone layer 213, 213' may be located closer to an outer surface of the tubular body 211. Preferably, electrical conductors (not shown in FIGS. 23A and 23B, but shown in FIGS. 24B, 24C, 25, and 26) are arranged in electrical communication with the adjustable flexure elements 212, 212'. In certain embodiments, at least one adjustable flexure element 212, 212' of the pair of adjustable flexure elements 212, 212' is independently controllable relative to at least one other adjustable flexure element 212, 212' of the pair of adjustable flexure elements 212, 212'. FIG. 23A shows the pair of adjustable flexure elements 212, 212' in a straightened state. FIG. 23B shows the pair of adjustable flexure elements 212, 212' each curved to the left, and FIG. 23C shows the pair of adjustable flexure elements 212, 212' each curved to the right.

FIG. 24A is a simplified schematic cross-sectional illustration of a portion of another guidewire device 220 in which angle or radius of curvature at one or more locations may be adjusted by applying current to electrically operable adjustable flexure elements 222A, 222A', 222B arranged in or on a tubular body 221. Each adjustable flexure element (e.g., 222A, 222A', 222B) includes a coating layer or backbone layer 223A, 223A', 223B (e.g., a metal) arranged in contact with an electrically responsive material 224A, 224A' (e.g., a piezoelectric material, an electroactive polymer, or a nitinol alloy). Multiple (e.g., first and second) pairs of adjustable flexure elements are provided, wherein each pair of adjustable flexure elements includes first and second opposing flexure elements arranged at different lateral positions relative to the tubular body 221. The second pair of flexure elements (including flexure element 222B and a corresponding flexure element, not shown) is arranged at a different longitudinal position along the tubular body 221 relative to the first pair of opposing flexure elements (222A, 222A'). As shown in FIG. 24A, the tubular body 221 includes a longitudinally extending flexible core 225, such as may include one or more wires, fibers, or similar elements. In certain embodiments, the flexible core 225 comprises an electrically conductive material (e.g., including one or more metal-containing wires) to enable resistive heating of the tubular body 221 to permit softening of the tubular body 221 to affect its stiffness properties. Although electrical conductors are not shown in FIG. 24A, it is to be appreciated that electrical conductors extending in a generally longitudinal direction may be operatively coupled to each adjustable flexure element 222A, 222A', 222B. FIG. 24B is a first cross-sectional illustration of the guidewire device 220 according to FIG. 24A, including a first pair of adjustable flexure elements 222A, 222A' each including two layers of material, such as a metal coating or backbone layer 223A, 223A' each arranged in contact with an electrically responsive adjustable flexure layer 224A, 224A', with a first group of electrical conductors 226 being configured to conduct electrical signals to one flexure layer 224A, and a second group of electrical conductors 226' being configured to conduct electrical signals to another flexure layer 224A'. FIG. 24B also shows the longitudinally extending flexible core 225 (e.g., one or more wires, fibers, or similar elements) centrally arranged within the tubular body 221. FIG. 24C is a second cross-sectional illustration of the guidewire device 220 of FIG. 24A, showing the core member 225 as well as the tubular body 221 containing a second pair of adjustable flexure elements 222B, 222B' each including two layers of material, such as a metal coating or backbone layer 223B, 223B' arranged in contact with an electrically responsive adjustable flexure layer 224B, 224B', with the first group of electrical conductors 226 being configured to conduct electrical signals to one flexure layer 224B, and the second group of electrical conductors 226' being configured to conduct electrical signals to the other flexure layer 224B'. The resulting guidewire device 220 permits each pair of adjustable flexure elements 224A-224A', 224B-224B' (and preferably each individual adjustable flexure element 224A, 224A', 224B, 224B') to be independently operated to enable adjustment of angle and/or curvature of the guidewire device 220 at multiple positions along its length. Although only two pairs of adjustable flexure elements 224A-224A', 224B-224B' are shown in FIG. 24A to 24C, it is to be appreciated that any suitable number of two, three, four, five or more pairs of adjustable flexure elements may be provided.

Consistent with the preceding discussion of FIGS. 23A-24C, in certain embodiments, a guidewire device includes a tubular body having a longitudinal axis, a first end, a second end, and an interior; and a plurality of adjustable flexure elements arranged in or on the tubular body; wherein the plurality of adjustable flexure elements are electrically operable to adjust an angle or curvature of the guidewire device between the first end and the second end. In certain embodiments, a plurality of circumferentially contractible fiber regions (e.g., a piezoelectric material, an electroactive polymer, or a nitinol alloy, not shown but described hereinafter in connection with FIGS. 28A-30) may be arranged in or on the tubular body, wherein each circumferentially contractible fiber region of the plurality of circumferentially contractible fiber regions is longitudinally spaced from each other circumferentially contractible fiber region. In certain embodiments, a plurality of radially contractible fiber regions (e.g., a piezoelectric material, an electroactive polymer, or a nitinol alloy, not shown but described hereinafter in connection with FIGS. 28A-30) may be arranged in or on the tubular body, wherein each radially contractible fiber region of the plurality of radially contractible fiber regions is longitudinally spaced from each other radially contractible fiber region. In certain embodiments, the tubular body includes a polymer adhesive, and the guidewire device includes at least one electrical conductor configured to be coupled with an electric power source for resistive heating of the polymer adhesive to adjust a stiffness property of the polymer adhesive.

FIG. 25 is a cross-sectional illustration of a portion of another guidewire device 230 (similar to the device 220 of FIGS. 24A-24C) including multiple pairs of adjustable flexure elements 232A-232A', 232B-232B' arranged in a tubular body 231, wherein first and second pairs of adjustable flexure elements 232A-232A', 232B-232B' are arranged at the same or a similar longitudinal position. Each pair of adjustable flexure elements 232A-232A', 232B-232B' includes first and second opposing flexure elements 232A-232A', 232B-232B' arranged at different lateral positions relative to the tubular body 231. Each adjustable flexure element 232A, 232A', 232B, 232B' may include a coating layer or backbone layer 233A, 233A', 233B, 233B' (e.g., a metal) arranged in contact with an electrically responsive material 234A, 234A', 234B, 234B' (e.g., a piezoelectric material, an electroactive polymer, or a nitinol alloy). As shown in FIG. 25, the tubular body 231 includes a longitudinally extending flexible core 235 (such as may include one or more wires, fibers, or similar elements) and further includes peripherally arranged groups of electrical conductors 236, 236' extending in a generally longitudinal direction, with different electrical conductors being operatively coupled with one or more different adjustable flexure elements 232A, 232A', 232B, 2326'.

FIG. 26 is a cross-sectional illustration of a portion of another guidewire device 240 (similar to the device 240 of FIG. 25) including multiple pairs of adjustable flexure elements 242A-242A', 242B-242B' arranged in a tubular body 241, wherein first and second pairs of adjustable flexure elements 242A-242A', 242B-242B' are arranged at the same or a similar longitudinal position. Each pair of adjustable flexure elements 242A-242A', 242B-242B' includes first and second opposing flexure elements 242A, 242A', 242B, 242B' arranged at different lateral positions relative to the tubular body 241. Each adjustable flexure element 242A, 242A', 242B, 242B' may include a coating layer or backbone layer 243A, 243A', 243B, 243B' (e.g., a metal) arranged in contact with an electrically responsive material 244A, 244A', 244B, 244B' (e.g., a piezoelectric material, an electroactive polymer, or a nitinol alloy). As shown in FIG. 25, the tubular body 241 includes a longitudinally extending flexible core 245 (such as may include one or more wires, fibers, or similar elements) and further includes groups of electrical conductors 246, 246' extending in a generally longitudinal direction, with different electrical conductors 246, 246' being operatively coupled with one or more different adjustable flexure elements 242A, 242A', 242B, 2426', wherein the electrical conductors 246, 246' are arranged generally between the flexible core 245 and the adjustable flexure elements 242A, 242A', 242B, 2426'.

Figures 27A, 27B, 27C:
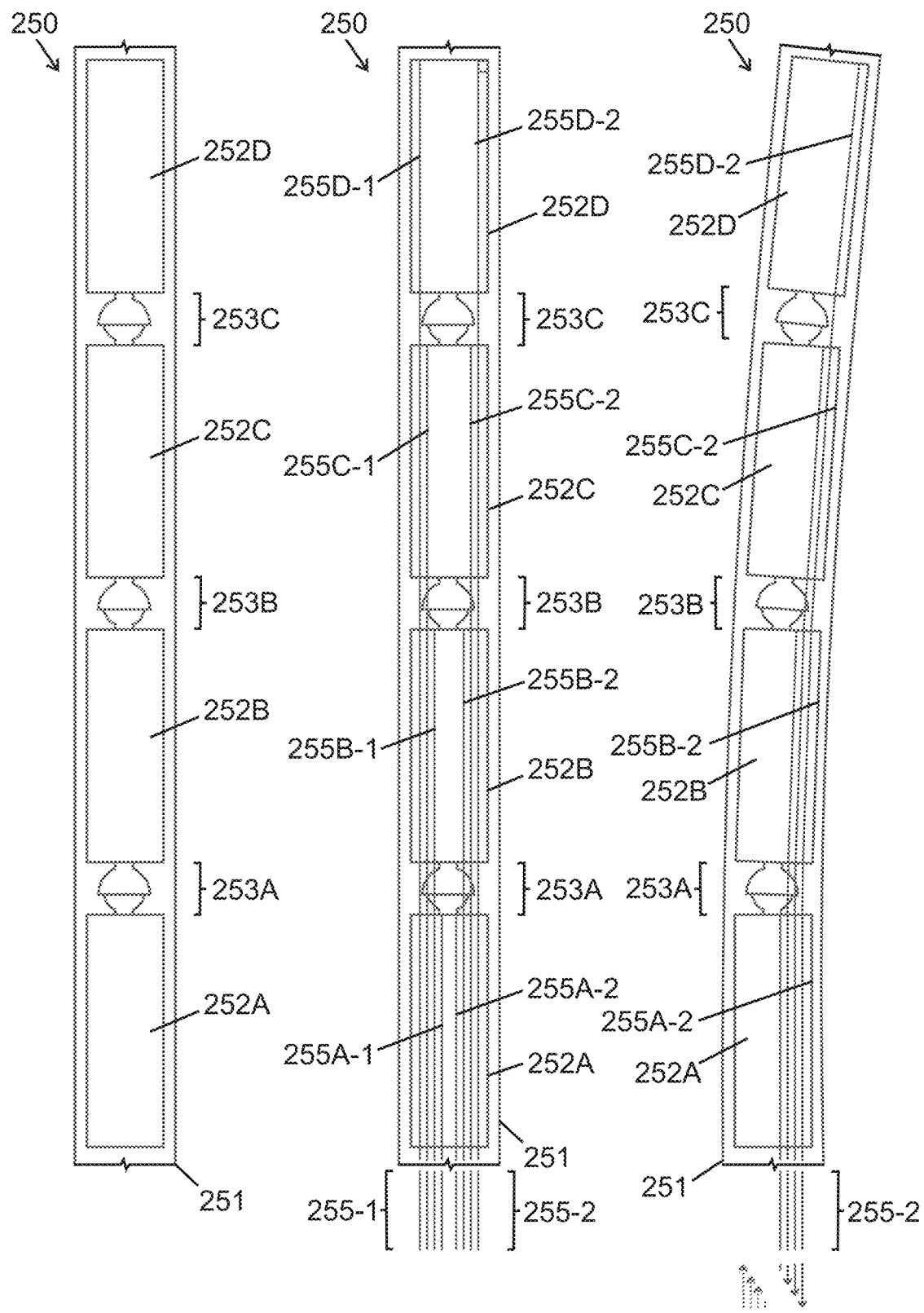
FIG. 27A is a simplified cross-sectional schematic illustration of a portion of a guidewire device including multiple body elements and multiple pivot joints that are sequentially arranged in a longitudinal direction within a tubular body, wherein each body element is connected to at least one other body element via at least one pivot joint, according to one embodiment of the present disclosure.
FIG. 27B is a cross-sectional schematic illustration of the portion of the guidewire device corresponding to FIG. 27A, with addition of tensile elements extending in a longitudinal direction within the tubular body.
FIG. 27C is a cross-sectional schematic view of a portion of the guidewire device corresponding to FIG. 27B, while omitting one (antagonist) set of guidewires for clarity, and showing another (agonist) set of guidewires following application of tension.

FIG. 27A is a simplified cross-sectional schematic illustration of a portion of a guidewire device 250 including multiple (e.g., four) body elements 252A-252D and multiple (e.g., three) pivot joints 253A-253C that are sequentially arranged in a longitudinal direction within a tubular body 251 (e.g., a tube), wherein each body element 252A-252D is connected to at least one other body element 252A-252D via at least one pivot joint 253A-253C. In certain embodiments, each pivot joint 253A-253C may include a ball and socket joint. FIG. 27B is a cross-sectional schematic illustration of the portion of the guidewire device 250 of FIG. 27A, with addition of tensile elements 255A-1, 255B-1, 255C-1, 255D-1, 255A-2, 255B-2, 255C-2, 255D-2 extending in a longitudinal direction within the tubular body structure 251. In certain embodiments, the tensile elements 255A-1, 255B-1, 255C-1, 255D-1, 255A-2, 255B-2, 255C-2, 255D-2 include wires, filaments, strands, fibers, or the like. In certain embodiments, tensile elements 255A-1, 255B-1, 255C-1, 255D-1, 255A-2, 255B-2, 255C-2, 255D-2 may include metal wires and/or fibrous strands of material such as small diameter fishing line. In certain embodiments, gel-spun polyethylene may be used, such as Berkley NanoFil monofilament/braid hybrid line, commercially available in a diameter as small as 0.008 inch (0.2 mm). Different tensile elements 255A-1, 255B-1, 255C-1, 255D-1, 255A-2, 255B-2, 255C-2, 255D-2 terminate at different body elements 252A-252D, and are separately operable to cause pivotal movement of different body elements 252A-252D, thereby permitting adjustment of an angle or curvature of the guidewire device 250 at multiple positions along the longitudinal axis. In certain embodiments, the tensile elements 255A-1, 255B-1, 255C-1, 255D-1, 255A-2, 255B-2, 255C-2, 255D-2 are operatively connected to a plurality of tensioning elements (e.g., motors, solenoids, actuators, or the like; not shown) configured to selectively apply tension to different tensile elements 255A-1, 255B-1, 255C-1, 255D-1, 255A-2, 255B-2, 255C-2, 255D-2. In certain embodiments, the plurality of tensioning elements is arranged beyond the first or second end of the tubular body structure 251. Certain tensile elements 255A-1, 255B-1, 255C-1, 255D-1 may be arranged in a first tensile element group 255-1, and other tensile elements 255A-2, 255B-2, 255C-2, 255D-2 may be arranged in a second tensile element group 255-2.

In certain embodiments, the tensile elements 255A-1, 255B-1, 255C-1, 255D-1, 255A-2, 255B-2, 255C-2, 255D-2 include at least one agonist tensile element (or group thereof, such as the second tensile element group 255-2) and at least one antagonist tensile element (or group thereof, such as the first tensile element group 255-1), wherein the at least one antagonist tensile element is configured to be operated to counteract the at least one agonist tensile element to control pivotal movement between different body elements 252A-252D. FIG. 27B shows the tensile elements 255A-1, 255B-1, 255C-1, 255D-1, 255A-2, 255B-2, 255C-2, 255D-2 without application of tensile force, with the guidewire device 250 in a straight configuration. FIG. 27C is a cross-sectional schematic illustration of a portion of the guidewire device 250 corresponding to FIG. 27B, while omitting (for clarity) the first tensile element group 255-1 of FIG. 27B that may serve as an antagonist tensile element, and showing the second tensile element group 255-2 serving as an agonist tensile element following application of tension (according to the tension profile at bottom) to the tensile elements 255A-2, 255B-2, 255C-2, 255D-2 using multiple tensioning elements (not shown). Selective application of tension to different tensile elements 255A-1, 255B-1, 255C-1, 255D-1, 255A-2, 255B-2, 255C-2, 255D-2 or groups thereof permits pivotal movement between different body elements 252A-252D, thereby permitting angle and/or curvature of the guidewire device 250 to be adjusted, preferably at multiple positions along its length.

With further reference to FIGS. 27B and 27C, in certain embodiments, a plurality of circumferentially contractible fiber regions (not shown but described hereinafter in connection with FIGS. 28A-30) is arranged in or on the tubular body structure 251, wherein each circumferentially contractible fiber region is longitudinally spaced from each other circumferentially contractible fiber region. In certain embodiments, a plurality of radially contractible fiber regions (not shown but described hereinafter in connection with FIGS. 28A-30) is arranged in or on the tubular body structure 251, wherein each radially contractible fiber region is longitudinally spaced from each other radially contractible fiber region. In certain embodiments, the tubular body structure 251 comprises a polymer adhesive, and the guidewire device 250 includes at least one electrical conductor (not shown) configured to be coupled with an electric power source for resistive heating of the polymer adhesive to adjust a stiffness property of the polymer adhesive.

Figure 28A:
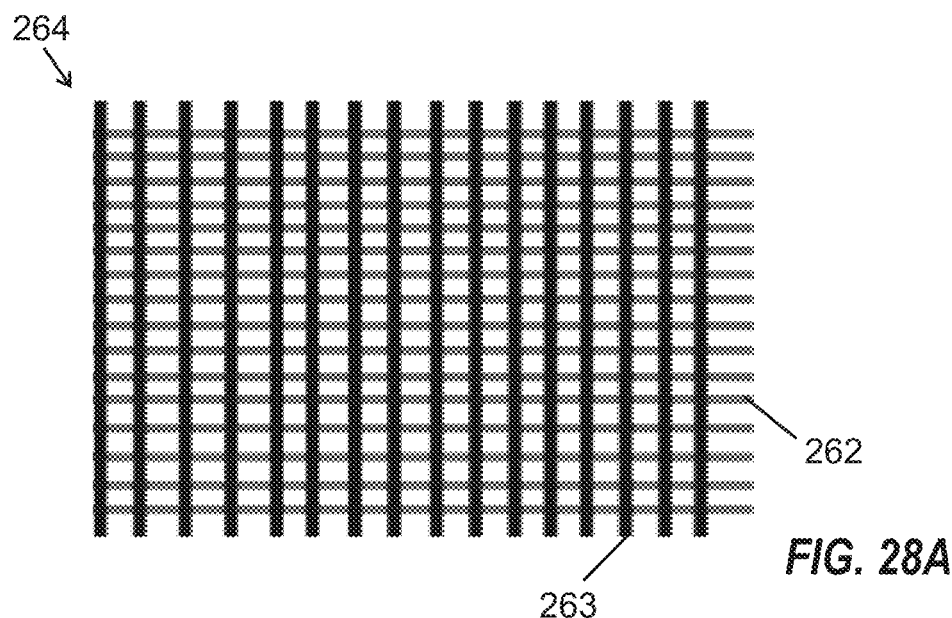
FIG. 28A is a grid of (horizontally arranged) longitudinally contractible fiber regions and (vertically arranged) circumferentially contractible fiber regions that may be incorporated into a guidewire device, according to one embodiment of the present disclosure.
Figure 28B:
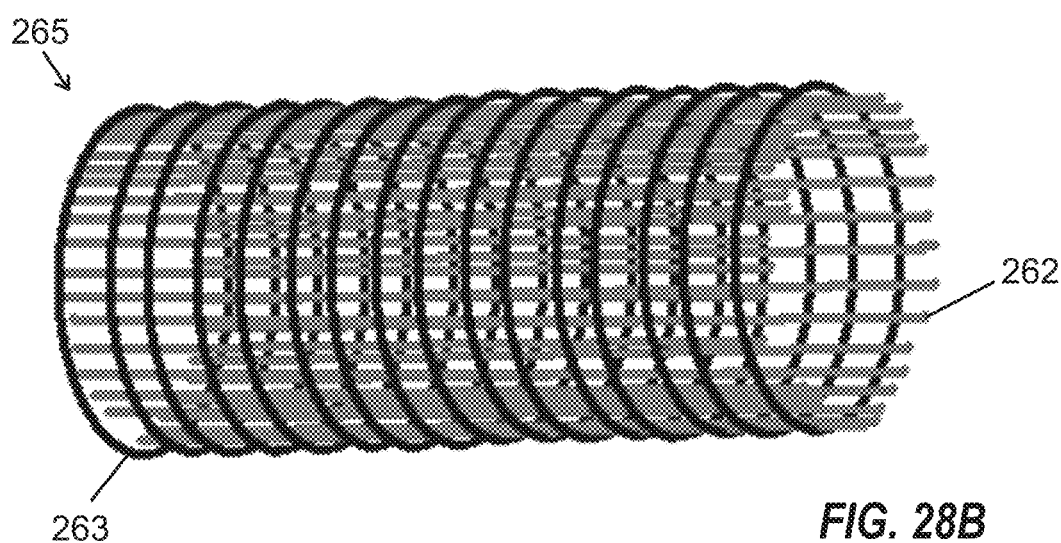
FIG. 28B is a perspective view illustration of a tubular structure of longitudinally contractible fiber regions and circumferentially contractible fiber regions obtained by rolling the grid of FIG. 28A into a tubular shape, according to one embodiment of the present disclosure.

FIG. 28A illustrates a grid 264 of (horizontally arranged) longitudinally contractible fiber regions 262 and (vertically arranged) circumferentially contractible fiber regions 263 that may be incorporated into a guidewire device. Each contractible fiber region 262, 263 may include a piezoelectric material, an electroactive polymer, and/or a nitinol alloy, and is preferably actuated with an electrical signal. FIG. 28B is a perspective view illustration of a tubular structure 265 of longitudinally contractible fiber regions 262 and circumferentially contractible fiber regions 263 obtained by rolling the grid 264 of FIG. 28A into a tubular shape. The tubular structure 265 of FIG. 28B may be incorporated into a tubular body (e.g., via molding, dipping, coating, or another suitable method), such as a tubular body 261 of a guidewire device 260 shown in the cross-sectional illustration of FIG. 28C. The guidewire device 260 includes longitudinally contractible fiber regions 262 and circumferentially contractible fiber regions 263 within the tubular body 261. In certain embodiments, the tubular body 261 may include polymer adhesive material. Although not shown in FIG. 28C, electrical conductors may extend in a generally longitudinal direction within the tubular body 261 to conduct electrical signals to various contractible fiber regions 262, 263. Each circumferentially contractible fiber region 263 of the plurality of circumferentially contractible fiber regions 263 is longitudinally spaced from each other circumferentially contractible fiber region 263. Actuation of different circumferentially contractible fiber regions 263 permits selective constriction of portions of the guidewire device 260, thereby adjusting local stiffness. Actuation of different longitudinally contractible fiber regions 262 permits an angle or curvature of the guidewire device 260 to be altered. In combination, control of the circumferentially contractible fiber regions 263 and the longitudinally contractible fiber regions 262 may permit both stiffness and angle or curvature of the guidewire device 260 to be adjusted at multiple locations along its length.

Figure 28C:
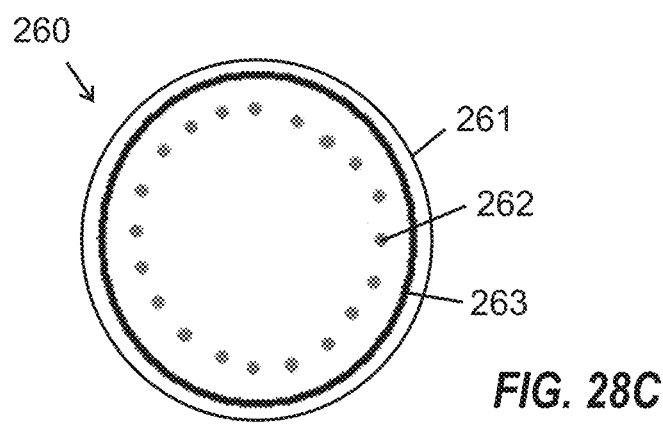
FIG. 28C is a cross-sectional view of a tubular body incorporating the tubular structure of FIG. 28B.
Figure 29:
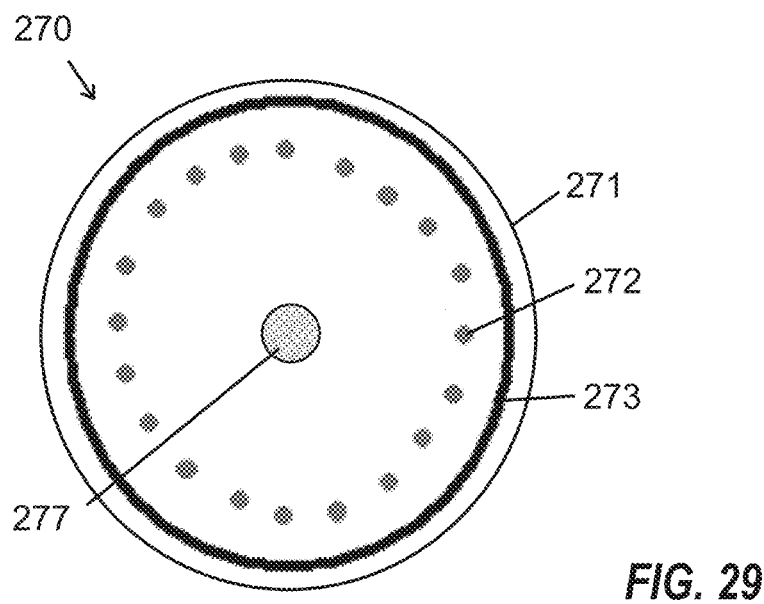
FIG. 29 is a cross-sectional illustration of at least a portion of a guidewire device similar to FIG. 28C, with addition of a longitudinally extending flexible core according to one embodiment of the present disclosure.

FIG. 29 is a cross-sectional illustration of at least a portion of a guidewire device 270 similar to the guidewire device 260 of FIG. 28C, but with addition of a longitudinally extending flexible core 277, such as may include one or more wires, fibers, or similar elements. The guidewire device 270 further includes longitudinally contractible fiber regions 272 and circumferentially contractible fiber regions 273 within a tubular body 271. In certain embodiments, the core 277 comprises an electrically conductive material (e.g., including one or more metal-containing wires) to enable resistive heating of the tubular body 271 to permit softening of the tubular body 271 to affect its stiffness properties.

Figure 30:
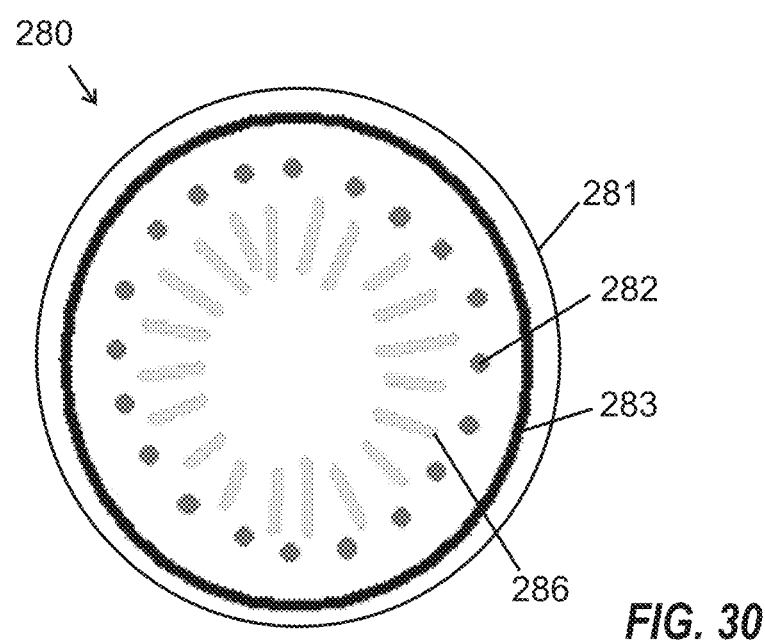
FIG. 30 is a cross-sectional illustration of at least a portion of a guidewire device similar to FIG. 28C, with addition of a plurality of radially contractible fiber regions arranged in or on the tubular body according to one embodiment of the present disclosure.

FIG. 30 is a cross-sectional illustration of at least a portion of a guidewire device 280 similar to the guidewire device 260 of FIG. 28C, but with addition of a plurality of radially contractible fiber regions 286 (e.g., a piezoelectric material, an electroactive polymer, or a nitinol alloy) arranged in or on a tubular body 281. The radially contractible fiber regions 286 resemble spokes of a bicycle wheel. Actuation of different radially contractible fiber regions 286 permits selective constriction of portions of the guidewire device 280, permitting stiffness of the guidewire device 280 to be locally adjusted. Multiple different radially contractible fiber regions 286 may be longitudinally spaced apart from one another and may be independently controlled. The guidewire device 280 further includes longitudinally contractible fiber regions 282 and circumferentially contractible fiber regions 283 within the tubular body 281. In certain embodiments, the tubular body 281 includes a polymer adhesive, and the guidewire device 280 includes at least one electrical conductor (not shown) configured to be coupled with an electric power source (not shown) for resistive heating of the polymer adhesive to adjust a stiffness property of the polymer adhesive.

Figure 31:
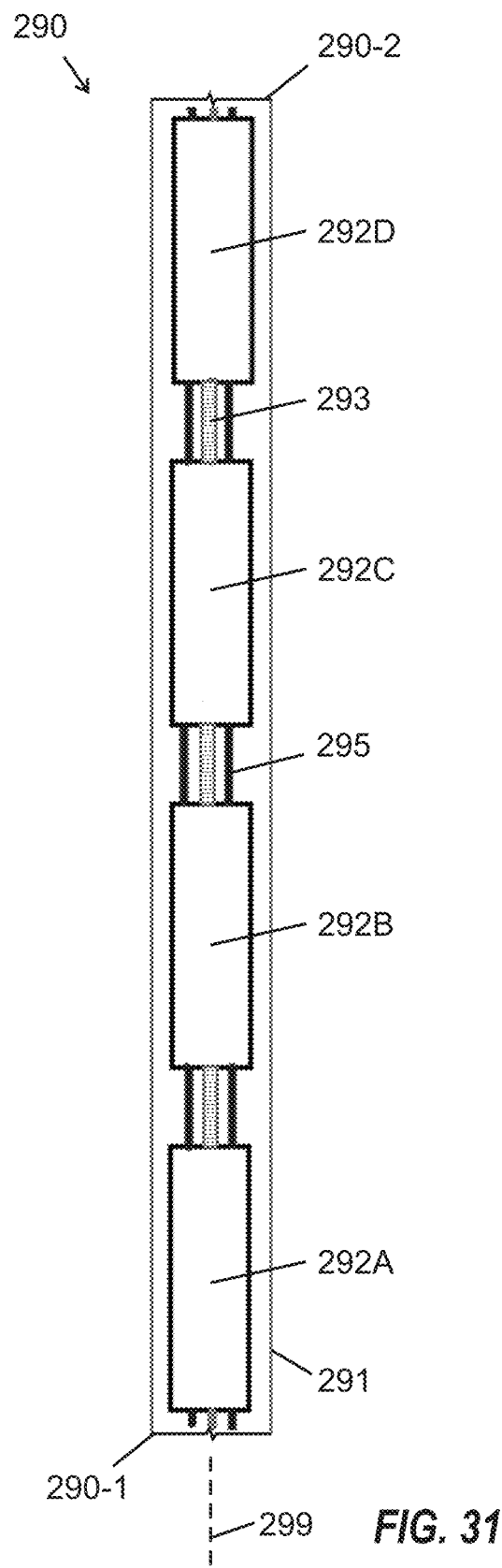
FIG. 31 is a cross-sectional schematic illustration of a portion of a guidewire device according to one embodiment of the present disclosure, including a longitudinal axis, a first end, a second end, and an interior, with a centrally arranged flexible guide wire or track arranged within the interior.

FIG. 31 is a cross-sectional schematic illustration of a portion of a guidewire device 290 including a longitudinal axis 299, a first end 290-1, a second end 290-2, and a tubular body 291 having an interior, with a centrally arranged flexible guide wire or track 293 (optionally including teeth or grooves) arranged within the interior. Multiple (e.g., four) translatable elements 292A-292D are arranged to independently translate along the flexible guide wire or track 293 parallel to the longitudinal axis 299. Each translatable element 292A-292D is electrically operable to be translated in a longitudinal direction and thereby adjust a stiffness, angle, or curvature of the guidewire device 290 between the first end 290-1 and the second end 290-2. In certain embodiments, each translatable element 292A-292D includes an electric motor unit. In certain embodiments, the electric motor unit of each translatable element 292A-292D is controllable by a signal of a different frequency from each other electric motor unit of the guidewire device 290. In this manner, a single pair of conductors 295 coupled to the motor of each translatable element 292A-292D may be used to separately control each motor. In certain embodiments, the flexible guide wire or track 293 includes a plurality of grooves or teeth, and each electric motor unit of the respective translatable elements 292A-292D includes an engagement element arranged to engage with the plurality of grooves or teeth. In certain embodiments, the tubular body 291 includes a polymer adhesive, and the guidewire device 290 includes at least one electrical conductor (not shown) configured to be coupled with an electric power source (not shown) for resistive heating of the polymer adhesive to adjust a stiffness property of the polymer adhesive.

Upon reading the following description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein and the claims that follow.

What is claimed is:

1. A guidewire device comprising:
   a tubular body having a longitudinal axis, a first end, a second end, and an interior;
   a plurality of longitudinally contractible fiber regions arranged in or on the tubular body, wherein each longitudinally contractible fiber region of the plurality of longitudinally contractible fiber regions is laterally spaced from each other longitudinally contractible fiber region;
   a plurality of circumferentially contractible fiber regions arranged in or on the tubular body, wherein each circumferentially contractible fiber region of the plurality of circumferentially contractible fiber regions is longitudinally spaced from each other circumferentially contractible fiber region and;
   a plurality of radially contractible fiber regions arranged in or on the tubular body;
   wherein each radially contractible fiber region of the plurality of radially contractible fiber regions is longitudinally spaced from each other radially contractible fiber region;
   wherein different longitudinally contractible fiber regions of the plurality of longitudinally contractible fiber regions are separately operable to adjust an angle or curvature of the guidewire device between the first end and the second end; and
   wherein different circumferentially contractible fiber regions of the plurality of circumferentially contractible fiber regions are separately operable to locally adjust a stiffness of the tubular body.

2. The guidewire device of claim 1, wherein each circumferentially contractible fiber region of the plurality of circumferentially contractible fiber regions comprises an electrically responsive material selected from the group consisting of a piezoelectric material, an electroactive polymer, and a nitinol alloy.

3. The guidewire device of claim 1, wherein each longitudinally contractible fiber region of the plurality of longitudinally contractible fiber regions comprises an electrically responsive material selected from the group consisting of a piezoelectric material, an electroactive polymer, and a nitinol alloy.

4. The guidewire device of claim 1, wherein each radially contractible fiber region of the plurality of radially contractible fiber regions comprises an electrically responsive material selected from the group consisting of a piezoelectric material, an electroactive polymer, and a nitinol alloy.

5. The guidewire device of claim 1, wherein the tubular body comprises a polymer adhesive, and the guidewire device includes at least one electrical conductor configured to be coupled with an electric power source for resistive heating of the polymer adhesive to adjust a stiffness property of the polymer adhesive.

6. The guidewire device of claim 1, comprising a metal coil spring or flexible metal sheath extending generally parallel to the longitudinal axis and surrounding at least a portion of the tubular body.

* * * * *